US012110342B2

(12) United States Patent
Weiner et al.

(10) Patent No.: US 12,110,342 B2
(45) Date of Patent: Oct. 8, 2024

(54) NUCLEIC ACID MONOCLONAL ANTIBODIES TARGETING PCSK9 AND METHODS OF USE

(71) Applicant: THE WISTAR INSTITUTE OF ANATOMY AND BIOLOGY, Philadelphia, PA (US)

(72) Inventors: David Weiner, Merion, PA (US); Makan Khoshnejad, Philadelphia, PA (US); Kar Muthumani, Cherry Hill, NJ (US); Ami Patel, Philadelphia, PA (US)

(73) Assignee: THE WISTAR INSTITUTE OF ANATOMY AND BIOLOGY, Philadelphia, PA (US)

( * ) Notice: Subject to any disclaimer, the term of this patent is extended or adjusted under 35 U.S.C. 154(b) by 0 days.

(21) Appl. No.: 16/966,513

(22) PCT Filed: Jan. 31, 2019

(86) PCT No.: PCT/US2019/015972
§ 371 (c)(1),
(2) Date: Jul. 31, 2020

(87) PCT Pub. No.: WO2019/152599
PCT Pub. Date: Aug. 8, 2019

(65) Prior Publication Data
US 2020/0362055 A1    Nov. 19, 2020

Related U.S. Application Data

(60) Provisional application No. 62/624,297, filed on Jan. 31, 2018.

(51) Int. Cl.
*C07K 16/40* (2006.01)
*A61P 3/06* (2006.01)
*A61K 39/00* (2006.01)

(52) U.S. Cl.
CPC ............. *C07K 16/40* (2013.01); *A61P 3/06* (2018.01); *A61K 2039/505* (2013.01)

(58) Field of Classification Search
None
See application file for complete search history.

(56) References Cited

U.S. PATENT DOCUMENTS

| 8,399,646 B2 * | 3/2013 | Liang ................. A61K 39/3955 536/23.53 |
| 2015/0087819 A1 * | 3/2015 | Jackson ................. C07K 16/40 536/23.53 |
| 2017/0096496 A1 | 4/2017 | Sleeman |
| 2017/0266282 A1 | 9/2017 | Weiner |

FOREIGN PATENT DOCUMENTS

| WO | 2015123325 | 8/2015 |
| WO | 2017165460 A1 | 9/2017 |

OTHER PUBLICATIONS

Schroeder et al. (J Allergy Clin Immunol 2010, 125:S41-S52).*
Lloyd et al. (Protein Engineering, Design & Selection 2009, 22:159-168).*
Rudikoff et al. (Proc Natl Acad Sci USA 1982 vol. 79 p. 1979).*
MacCallum et al. (J. Mol. Biol. 1996 262, 732-745).*
Pascalis et al. (The Journal of Immunology (2002) 169, 3076-3084).*
Casset et al. (BBRC 2003, 307:198-205).*
Vajdos et al. (J. Mol. Biol. (2002) 320, 415-428).*
Chen et al. (J. Mol. Bio. (1999) 293, 865-881).*
Wu et al. (J. Mol. Biol. (1999) 294, 151-162).*
Padlan et al. (PNAS 1989, 86:5938-5942).*
Lamminmaki et al. (JBC 2001, 276:36687-36694).*
Piche-Nicholas et al. MABS 2018, 10:81-94.*
Abifadel, M, Varret, M, Rabes, J, Allard, D, Ouguerram, K, Devillers, M, et al. (2003). Mutations in PCSK9 cause autosomal dominant hypercholesterolemia. Nat Genet. 34: 154-156.
Alghamdi, RH, O'Reilly, P, Lu, C, Gomes, J, Lagace, TA and Basak, A (2015). LDL-R promoting activity of peptides derived from human PCSK9 catalytic domain (153-421): design, synthesis and biochemical evaluation. Eur. J. Med. Chem. 92: 890-907.
American Stroke Association (2017). Heart Disease and Stroke Statistics—2017 Update: A Report From the American Heart Association. Circulation 135: e146-e603.
Arrieta, A, Hong, JC, Khera, R, Virani, SS, Krumholz, HM and Nasir, K (2017). Updated cost-effectiveness assessments of PCSK9 inhibitors from the perspectives of the health system and private payers: Insights derived from the Fourier Trial. JAMA Cardiol. 2: 1369-1374.
Basak, A, Shervani, NJ, Mbikay, M and Kolajova, M (2008). Recombinant proprotein convertase 4 ( PC4 ) from Leishmania tarentolae expression system : Purification , biochemical study and inhibitor design. Protein Expr. Purif. 60: 117-126.
Bassi, DE, Zhang, J, Cenna, J, Litwin, S, Cukierman, E and Klein-szanto, AJP (2010). Proprotein Convertase Inhibition Results in Decreased Skin Cell Proliferation, Tumorigenesis, and Metastasis. Neoplasia 12: 516-526.
Bays, H, Gaudet, D, Weiss, R, Ruiz, JL, Watts, GF, Gouni-Berthold, I, et al. (2015). Alirocumab as add-on to atorvastatin versus other lipid treatment strategies: Odyssey Options I randomized trial. J. Clin. Endocrinol. Metab. 100: 3140-3148.
Becker, GL, Lu, Y, Hardes, K, Strehlow, B, Levesque, C, Lindberg, I, et al. (2012). Highly Potent Inhibitors of Proprotein Convertase Furin as Potential Drugs for Treatment of Infectious Diseases. J. Biol. Chem. 287: 21992-22003.

(Continued)

*Primary Examiner* — Sharon X Wen
(74) *Attorney, Agent, or Firm* — Riverside Law LLP

(57) ABSTRACT

Disclosed herein is a composition including a recombinant nucleic acid sequence that encodes an antibody or fragment thereof that targets PCSK9. The disclosure also provides a method of preventing and/or treating disease, such as cardiovascular disease or hypercholesterolemia, in a subject using the composition of the invention.

14 Claims, 12 Drawing Sheets

Specification includes a Sequence Listing.

(56) References Cited

OTHER PUBLICATIONS

Becker, GL, Sielaff, F, Than, ME, Lindberg, I, Routhier, S, Day, R, et al. (2010). Potent Inhibitors of Furin and Furin-like Proprotein Convertases Containing Decarboxylated P1 Arginine Mimetics. J Med Chem. 53: 1067-1075.

Benjannet, S, Rhainds, D, Essalmani, R, Mayne, J, Wickham, L, Jin, W, et al. (2004). NARC-1/PCSK9 and its natural mutants: zymogen cleavage and effects on the low density lipoprotein (LDL) receptor and LDL cholesterol. J. Biol. Chem. 279: 48865-48875.

Blanchet, M, Sureau, C, Guévin, C, Seidah, NG and Labonté, P (2015). SKI-1 / S1P inhibitor PF-429242 impairs the onset of HCV infection. Antiviral Res. 115: 94-104.

Bruckert, E, Hayem, G, Dejager, S, Yau, C and Bégaud, B (2005). Mild to moderate muscular symptoms with high-dosage statin therapy in hyperlipidemic patients—The PRIMO study. Cardiovasc. Drugs Ther. 19: 403-414.

Cameron, J, Ranheim, T, Kulseth, MA, Leren, TP and Berge, KE (2008). Berberine decreases PCSK9 expression in HepG2 cells. Atherosclerosis 201: 266-273.

Cannon, CP, Cariou, B, Blom, D, McKenney, JM, Lorenzato, C, Pordy, R, et al. (2015). Efficacy and safety of alirocumab in high cardiovascular risk patients with inadequately controlled hypercholesterolaemia on maximally tolerated doses of statins: The Odyssey Combo II randomized controlled trial. Eur. Heart J. 36: 1186-1194.

Chan, JCY, Piper, DE, Cao, Q, Liu, D, King, C, Wang, W, et al. (2009). A proprotein convertase subtilisin / kexin type 9 neutralizing antibody reduces serum cholesterol in mice and nonhuman primates. Proc. Natl. Acad. Sci. USA 106: 9820-9825.

Cohen, J, Pertsemlidis, A, Kotowski, IK, Graham, R, Garcia, CK and Hobbs, HH (2005). Low LDL cholesterol in individuals of African descent resulting from frequent nonsense mutations in PCSK9. Nat Genet. 37: 161-165.

Colhoun, HM, Robinson, JG, Farnier, M, Cariou, B, Blom, D, Kereiakes, DJ, et al. (2014). Efficacy and safety of alirocumab, a fully human PCSK9 monoclonal antibody, in high cardiovascular risk patients with poorly controlled hypercholesterolemia on maximally tolerated doses of statins: rationale and design of the Odyssey Combo I and II trials. BMC Cardiovasc. Disord. 14: 121.

Coppola, JM, Bhojani, MS, Ross, BD and Rehemtulla, A (2008). A Small-Molecule Furin Inhibitor Inhibits Cancer Cell Motility. Neoplasia. 10: 363-370.

Crossey, E, Amar, MJA, Sampson, M, Peabody, J, Schiller, JT, Chackerian, B, et al. (2015). A cholesterol-lowering VLP vaccine that targets PCSK9. Vaccine 33: 5747-5755.

Cunningham, D, Danley, DE, Geoghegan, KF, Griffor, MC, Hawkins, JL, Subashi, TA, et al. (2007). Structural and biophysical studies of PCSK9 and its mutants linked to familial hypercholesterolemia. Nat. Struct. Mol. Biol. 14: 413-419.

Dong, B, Li, H, Singh, AB, Cao, A and Liu, J (2015). Inhibition of PCSK9 transcription by berberine involves down-regulation of hepatic HNF1α protein expression through the ubiquitin-proteasome degradation pathway. J. Biol. Chem. 290: 4047-4058.

Elliott, STC, Kallewaard, NL, Benjamin, E, Wachter-Rosati, L, McAuliffe, JM, Patel, A, et al. (2017). DMAb inoculation of synthetic cross reactive antibodies protects against lethal influenza A and B infections. npj Vaccines 2.

Farnier, M, Jones, P, Severance, R, Averna, M, Steinhagen-Thiessen, E, Colhoun, HM, et al. (2016). Efficacy and safety of adding alirocumab to rosuvastatin versus adding ezetimibe or doubling the rosuvastatin dose in high cardiovascular-risk patients: The Odyssey Options II randomized trial. Atherosclerosis 244: 138-146.

Fitzgerald, K, White, S, Borodovsky, A, Bettencourt, BR, Strahs, A, Clausen, V, et al. (2017). A Highly Durable RNAi Therapeutic Inhibitor of PCSK9. N. Engl. J. Med. 376: 41-51. 53.

Flingai, S, Plummer, EM, Patel, A, Shresta, S, Mendoza, JM, Broderick, KE, et al. (2015). Protection against dengue disease by synthetic nucleic acid antibody prophylaxis/immunotherapy. Sci. Rep. 5: Article-No. 12616.

Frank-kamenetsky, M, Grefhorst, A, Anderson, NN, Racie, TS, Bramlage, B, Akinc, A, et al. (2008). Therapeutic RNAi targeting PCSK9 acutely lowers plasma cholesterol in rodents and LDL cholesterol in nonhuman primates. Proc. Natl. Acad. Sci. USA. 105: 11915-20.

Galabova, G, Brunner, S, Winsauer, G, Juno, C, Wanko, B, Mairhofer, A, et al. (2014). Peptide-based anti-PCSK9 vaccines-an approach for long-term LDLc management. PLoS One 9: 1-18.

Ginsberg, HN, Rader, DJ, Raal, FJ, Guyton, JR, Baccara-Dinet, MT, Lorenzato, C, et al. (2016). Efficacy and Safety of Alirocumab in Patients with Heterozygous Familial Hypercholesterolemia and LDL-C of 160 mg/dl or Higher. Cardiovasc. Drugs Ther. 30: 473-483.

Goldstein, JL and Brown, MS (2015). A Century of Cholesterol and Coronaries: From Plaques to Genes to Statins. Cell 161: 161-172.

Gupta, N, Fisker, N, Asselin, M, Lindholm, M, Rosenbohm, C, Seidah, NG, et al. (2010). A Locked Nucleic Acid Antisense Oligonucleotide ( LNA ) Silences PCSK9 and Enhances LDLR Expression In Vitro and In Vivo. PLoS One. 5: e10682.

Hardes, K, Becker, GL, Lu, Y, Dahms, SO, Kchler, S, Beyer, W, et al. (2015). Novel Furin Inhibitors with Potent Anti-infectious Activity. ChemMedChem. 10: 1218-1231.

Hyrina, A, Meng, F, Mcarthur, SJ, Eivemark, S and Nabi, IR (2017). Human Subtilisin Kexin Isozyme-1 ( SKI-1 )/ Site-1 Protease ( S1P ) regulates cytoplasmic lipid droplet abundance : A potential target for indirect-acting anti-dengue virus agents. PLoS One. 12: e0174963.

Inocencio, NM, Sucic, JF, Moehring, JM, Spence, MJ and Moehring, TJ (1997). Endoprotease Activities Other Than Furin and PACE4 with a Role in Processing of HIV-I gp160 Glycoproteins in CHO-K1 Cells. J. Biol. Chem. 272: 1344-1348.

Institute for Clinical and Economic Review (2015). PCSK9 Inhibitors for Treatment of High Cholesterol: Effectiveness, Value, and ValueBased Price Benchmarks Draft Report. Inst. Clin. Econ. Rev.: 1-116.

James M. Backes, Janelle F. Ruisinger, Cheryl A. Gibson, PMM (2017). Statin-associated muscle symptoms—Managing the highly intolerant. J. Clin. Lipidol. 11: 24-33. 79. Gusarova, V, Howard, VG, Okamoto, H, Koehler-Stec, E-M, Papadopoulos, N, Murphy, AJ, et al. (2012). Reduction of LDL cholesterol by a monoclonal antibody to PCSK9 in rodents and nonhuman primates. Clin. Lipidol. 7: 737-743.

Kotowski, IK, Pertsemlidis, A, Luke, A, Cooper, RS, Vega, GL, Cohen, JC, et al. (2006). A Spectrum of PCSK9 Alleles Contributes to Plasma Levels of Low-Density Lipoprotein Cholesterol. Am. J. Hum. Genet. 78: 410-422.

Landlinger, C, Pouwer, MG, Juno, C, Hoorn, WA Van Der, Pieterman, EJ, Jukema, JW, et al. (2017). The AT04A vaccine against proprotein convertase subtilisin/kexin type 9 reduces total cholesterol, vascular inflammation, and atherosclerosis in APOE* 3Leiden. CETP mice. Eur. Heart J. 38: 2499-2507.

Levesque, C, Couture, F, Kwiatkowska, A, Desjardins, R, Guerin, B, Neugebauer, WA, et al. (2015). PACE4 inhibitors and their peptidomimetic analogs block prostate cancer tumor progression through quiescence induction, increased apoptosis and impaired neovascularisation. Oncotarget. 6: 3680-93.

Levesque, C, Fuge, M, Routhier, S, Moussette, P, Prahl, A, Lammek, B, et al. (2012). The Multi-Leu Peptide Inhibitor Discriminates Between PACE4 and Furin And Exhibits Antiproliferative Effects On Prostate Cancer Cells. J Med Chem. 55: 10501-11.

Li, H, Dong, B, Park, SW, Lee, HS, Chen, W and Liu, J (2009). Hepatocyte nuclear factor 1 plays a critical role in PCSK9 gene transcription and regulation by the natural hypocholesterolemic compound berberine. J. Biol. Chem. 284: 28885-28895.

Liang, H, Chaparro-riggers, J, Strop, P, Geng, T, Sutton, JE, Tsai, D, et al. (2012). Proprotein Convertase Subtilisin / Kexin Type 9 Antagonism Reduces Low-Density Lipoprotein Cholesterol in Statin-Treated Hypercholesterolemic Nonhuman Primates. J. Pharmacol. Exp. Ther. 340: 228-236.

(56) References Cited

OTHER PUBLICATIONS

Lindholm, MW, Elmén, J, Fisker, N, Hansen, HF, Persson, R, Møller, MR, et al. (2009). PCSK9 LNA Antisense Oligonucleotides Induce Sustained Reduction of LDL Cholesterol in Nonhuman Primates. Mol. Ther. 20: 376-381.

Ma, Y, Fan, W, Rao, S, Gao, L, Bei, Z and Xu, S (2014). Effect of Furin inhibitor on lung adenocarcinoma cell growth and metastasis. Cancer Cell Int. 14: 1-6.

Maxwell, KN and Breslow, JL (2004). Adenoviral-mediated expression of Pcsk9 in mice results in a low-density lipoprotein receptor knockout phenotype. Proc. Natl. Acad. Sci. USA. 101: 7100-5.

Mbikay M, Tadros H, Ishida N, Lerner CP, De Lamirande E, Chen A, El-Alfy M, Clermont Y, Seidah NG, Chrétien M, Gagnon C, Simpson EM. Impaired fertility in mice deficient for the testicular germ-cell protease PC4. Proc Natl Acad Sci U S A. Jun. 24, 1997;94(13):6842-6.

Mitchell, T, Chao, G, Sitkoff, D, Lo, F, Monshizadegan, H, Meyers, D, et al. (2014). Pharmacologic profile of the Adnectin BMS-962476, a small protein biologic alternative to PCSK9 antibodies for low-density lipoprotein lowering. J. Pharmacol. Exp. Ther. 350: 412-24.

Muthumani, K, Block, P, Flingai, S, Muruganantham, N, Chaaithanya, IK, Tingey, C, et al. (2016). Rapid and Long-Term Immunity Elicited by DNA-Encoded Antibody Prophylaxis and DNA Vaccination Against Chikungunya Virus. J. Infect. Dis. 214: 369-378.

Muthumani, K, Marnin, L, Kudchodkar, SB, Perales-Puchalt, A, Choi, H, Agarwal, S, et al. (2017). Novel prostate cancer immunotherapy with a DNA-encoded anti-prostate-specific membrane antigen monoclonal antibody. Cancer Immunol. Immunother. 66: 1577-1588.

Nelson, RH (2013). Hyperlipidemia as a Risk Factor for Cardiovascular Disease. Prim. Care 40: 195-211.

Ni, YG, Condra, JH, Orsatti, L, Shen, X, Di Marco, S, Pandit, S, et al. (2010). A proprotein convertase subtilisin-like/ kexin type 9 (PCSK9) C-terminal domain antibody antigen-binding fragment inhibits PCSK9 internalization and restores low density lipoprotein uptake. J. Biol. Chem. 285: 12882-12891.

Ni, YG, Marco, S Di, Condra, JH, Peterson, LB, Wang, W, Wang, F, et al. (2011). A PCSK9-binding antibody that structurally mimics the EGF ( A ) domain of LDL-receptor reduces LDL cholesterol in vivo. J. Lipid Res. 52: 78-86.

Nissen, SE, Dent-Acosta, RE, Rosenson, RS, Stroes, E, Sattar, N, Preiss, D, et al. (2016). Comparison of PCSK9 Inhibitor Evolocumab vs Ezetimibe in Statin-Intolerant Patients: Design of the Goal Achievement after Utilizing an Anti-PCSK9 Antibody in Statin-Intolerant Subjects 3 (GAUSS-3) Trial. Clin. Cardiol. 39: 137-144.

Olmstead, AD, Knecht, W, Lazarov, I and Dixit, SB (2012). Human Subtilase SKI-1 / S1P Is a Master Regulator of the HCV Lifecycle and a Potential Host Cell Target for Developing Indirect-Acting Antiviral Agents. PLoS Pathog. 8: e1002468.

Ozden, S, Lucas-hourani, M, Ceccaldi, P, Basak, A, Valentine, M, Benjannet, S, et al. (2008). Inhibition of Chikungunya virus infection in cultured human muscle cells by furin inhibitors: impairment of the maturation of the E2 surface glycoprotein. J. Biol. Chem. 283: 21899-21908.

Park, SW, Moon, Y and Horton, JD (2004). Post-transcriptional Regulation of Low Density Lipoprotein Receptor Protein by Proprotein Convertase Subtilisin/Kexin Type 9a in Mouse Liver. J. Biol. Chem. 279: 50630-50638.

Patel, A, Digiandomenico, A, Keller, AE, Smith, TRF, Park, DH, Ramos, S, et al. (2017). An engineered bispecific DNA-encoded IgG antibody protects against Pseudomonas aeruginosa in a pneumonia challenge model. Nat. Commun. 8.

Paul D. Thompson, Priscilla Clarkson, RHK (2003). Statin-Associated Myopathy. JAMA 289: 1681-1690.

Perak, AM, Ning, H, De Ferranti, SD, Gooding, HC, Wilkins, JT and Lloyd-Jones, DM (2016). Long-term risk of atherosclerotic cardiovascular disease in US adults with the familial hypercholesterolemia phenotype. Circulation 134: 9-19.

Petersen, DN, Hawkins, J, Ruangsiriluk, W, Stevens, KA, Maguire, BA, O'Connell, TN, et al. (2016). A Small-Molecule Anti-secretagogue of PCSK9 Targets the 80S Ribosome to Inhibit PCSK9 Protein Translation. Cell Chem. Biol. 23: 1362-1371.

Qian, LJ, Gao, Y, Zhang, YM, Chu, M, Yao, J and Xu, D (2017). Therapeutic efficacy and safety of PCSK9-monoclonal antibodies on familial hypercholesterolemia and statin-intolerant patients: A meta-analysis of 15 randomized controlled trials. Sci. Rep. 7: 238.

Raal, FJ, Giugliano, RP, Sabatine, MS, Koren, MJ, Langslet, G, Bays, H, et al. (2014). Reduction in lipoprotein(a) with PCSK9 monoclonal antibody evolocumab (AMG 145): A pooled analysis of more than 1,300 patients in 4 phase II trials. J. Am. Coll. Cardiol. 63: 1278-1288.

Raal, FJ, Stein, EA, Dufour, R, Turner, T, Civeira, F, Burgess, L, et al. (2015). PCSK9 inhibition with evolocumab (AMG 145) in heterozygous familial hypercholesterolaemia (Rutherford-2): A randomised, double-blind, placebo-controlled trial. Lancet 385: 331-340.

Repas, T and Tanner, J (2014). Preventing Early Cardiovascular Death in Patients With Familial Hypercholesterolemia. J. Am. Osteopath. Assoc. 114: 99-108.

Ridker, PM, Amarenco, P, Brunell, R, Glynn, RJ, Jukema, JW, Kastelein, JJP, et al. (2016). Evaluating bococizumab, a monoclonal antibody to PCSK9, on lipid levels and clinical events in broad patient groups with and without prior cardiovascular events: Rationale and design of the Studies of PCSK9 Inhibition and the Reduction of vascular Events . Am. Heart J. 178: 135-144.

Roy, S (2014). Atherosclerotic cardiovascular disease risk and evidence-based management of cholesterol. N. Am. J. Med. Sci. 6: 191-198.

Scamuffa, N, Siegfried, G, Bontemps, Y, Ma, L, Basak, A, Cherel, G, et al. (2008). Selective inhibition of proprotein convertases represses the metastatic potential of human colorectal tumor cells. J. Clin. Invest. 118: 352-63.

Seidah, NG and Prat, A (2012). The biology and therapeutic targeting of the proprotein convertases. Nat. Rev. Drug Discov. 11: 367-383.

Seidah, NG, Benjannet, S, Wickham, L, Marcinkiewicz, J, Stifani, S, Basak, A, et al. (2002). The secretory proprotein convertase neural Liver regeneration and neuronal differentiation. Proc. Natl. Acad. Sci. USA. 1: 928-933.

Shan, LX, Pang, L, Zhang, R, Murgolo, NJ, Lan, H and Hedrick, JA (2008). PCSK9 binds to multiple receptors and can be functionally inhibited by an EGF-A peptide. Biochem. Biophys. Res. Commun. 375: 69-73.

Stein, EA, Honarpour, N, Wasserman, SM, Xu, F, Scott, R and Raal, FJ (2013). Effect of the proprotein convertase subtilisin/kexin 9 monoclonal antibody, AMG 145, in homozygous familial hypercholesterolemia. Circulation 128, 2113-2120pp.

Stein, EA, Mellis, S, Yancopoulos, GD, Stahl, N, Logan, D, Smith, WB, et al. (2012). Effect of a monoclonal antibody to PCSK9 on LDL cholesterol. N. Engl. J. Med. 366: 1108-18.

Tebas, P, Roberts, CC, Muthumani, K, Reuschel, EL, Kudchodkar, SB, Zaidi, FI, et al. Safety and Immunogenicity of an Anti-Zika Virus DNA Vaccine. N Engl J Med. Sep. 16, 2021;385(12):e35.

Timms, KM, Wagner, S, Samuels, ME, Forbey, K, Goldfine, H, Jammulapati, S, et al. (2004). A mutation in PCSK9 causing autosomal-dominant hypercholesterolemia in a Utah pedigree. Hum Genet. 114: 349-353.

Trimble, CL, Morrow, MP, Kraynyak, KA, Shen, X, Dallas, M, Yan, J, et al. (2015). Safety, efficacy, and immunogenicity of VGX-3100, a therapeutic synthetic DNA vaccine targeting human papillomavirus 16 and 18 E6 and E7 proteins for cervical intraepithelial neoplasia 2/3: A randomised, double-blind, placebo-controlled phase 2b trial. Lancet 386: 2078-2088.

Van Poelgeest, EP, Hodges, MR, Moerland, M, Tessier, Y, Levin, AA, Persson, R, et al. (2015). Antisense-mediated reduction of proprotein convertase subtilisin/kexin type 9 (PCSK9): A first-in-human randomized, placebo-controlled trial. Br. J. Clin. Pharmacol. 80: 1350-1361.

Watanabe, M, Hirano, A, Stenglein, S, Nelson, JAY, Thomas, G and Wong, TC (1995). Engineered Serine Protease Inhibitor Prevents Furin-Catalyzed Activation of the Fusion Glycoprotein and Production of Infectious Measles Virus. J. Virol. 69: 3206-3210.

(56) References Cited

OTHER PUBLICATIONS

Xu, Z, Wise, MC, Choi, H, Perales-Puchalt, A, Patel, A, Tello-Ruiz, E, et al. (2018). Synthetic DNA delivery by electroporation promotes robust in vivo sulfation of broadly neutralizing anti-HIV immunoadhesin eCD4-lg. EBioMedicine 35: 97-105.

Yamamoto, T, Harada-Shiba, M, Nakatani, M, Wada, S, Yasuhara, H, Narukawa, K, et al. (2012). Cholesterol-lowering Action of BNA-based Antisense Oligonucleotides Targeting PCSK9 in Atherogenic Diet-induced Hypercholesterolemic Mice. Mol. Ther. Nucleic Acids 1: e22.

Zhang, H, Plutzky, J, Skentzos, S, Morrison, F, Mar, P, Shubina, M, et al. (2013). Discontinuation of statins in routine care settings, A cohort study. Ann. Intern. Med. 158: 526-534.

Zhang, L, McCabe, T, Condra, JH, Ni, YG, Peterson, LB, Wang, W, et al. (2012). An anti-PCSK9 antibody reduces LDL-cholesterol on top of a statin and suppresses hepatocyte srebp-regulated genes. Int. J. Biol. Sci. 8: 310-327.

Zhang, Y, Eigenbrot, C, Zhou, L, Shia, S, Li, W, Quan, C, et al. (2014). Identification of a small peptide that inhibits PCSK9 protein binding to the low density lipoprotein receptor. J. Biol. Chem. 289: 942-955.

\* cited by examiner

SEQUENCE LISTING

```
<160> NUMBER OF SEQ ID NOS: 8

<210> SEQ ID NO 1
<211> LENGTH: 714
<212> TYPE: PRT
<213> ORGANISM: Artificial Sequence
<220> FEATURE:
```

```
<223> OTHER INFORMATION: Mouse PCSK9 DMAb

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Ala Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser Ala Lys Thr Thr Ala Pro Ser
        115                 120                 125

Val Tyr Pro Leu Ala Pro Val Cys Gly Asp Thr Thr Gly Ser Ser Val
    130                 135                 140

Thr Leu Gly Cys Leu Val Lys Gly Tyr Phe Pro Glu Pro Val Thr Leu
145                 150                 155                 160

Thr Trp Asn Ser Gly Ser Leu Ser Ser Gly Val His Thr Phe Pro Ala
                165                 170                 175

Val Leu Gln Ser Asp Leu Tyr Thr Leu Ser Ser Ser Val Thr Val Thr
            180                 185                 190

Ser Ser Thr Trp Pro Ser Gln Ser Ile Thr Cys Asn Val Ala His Pro
        195                 200                 205

Ala Ser Ser Thr Lys Val Asp Lys Lys Ile Glu Pro Arg Gly Pro Thr
    210                 215                 220

Ile Lys Pro Cys Pro Pro Cys Lys Cys Pro Ala Pro Asn Leu Leu Gly
225                 230                 235                 240

Gly Pro Ser Val Phe Ile Phe Pro Pro Lys Ile Lys Asp Val Leu Met
                245                 250                 255

Ile Ser Leu Ser Pro Ile Val Thr Cys Val Val Val Asp Val Ser Glu
            260                 265                 270

Asp Asp Pro Asp Val Gln Ile Ser Trp Phe Val Asn Asn Val Glu Val
        275                 280                 285

His Thr Ala Gln Thr Gln Thr His Arg Glu Asp Tyr Asn Ser Thr Leu
    290                 295                 300

Arg Val Val Ser Ala Leu Pro Ile Gln His Gln Asp Trp Met Ser Gly
305                 310                 315                 320

Lys Glu Phe Lys Cys Lys Val Asn Asn Lys Asp Leu Pro Ala Pro Ile
                325                 330                 335

Glu Arg Thr Ile Ser Lys Pro Lys Gly Ser Val Arg Ala Pro Gln Val
            340                 345                 350

Tyr Val Leu Pro Pro Pro Glu Glu Glu Met Thr Lys Lys Gln Val Thr
        355                 360                 365

Leu Thr Cys Met Val Thr Asp Phe Met Pro Glu Asp Ile Tyr Val Glu
    370                 375                 380

Trp Thr Asn Asn Gly Lys Thr Glu Leu Asn Tyr Lys Asn Thr Glu Pro
385                 390                 395                 400
```

| | | | | | | | | | | | |
|---|---|---|---|---|---|---|---|---|---|---|---|
|Val|Leu|Asp|Ser|Asp|Gly|Ser|Tyr|Phe|Met|Tyr|Ser|Lys|Leu|Arg|Val|
| | | | |405| | | |410| | | |415| | | |

Val Leu Asp Ser Asp Gly Ser Tyr Phe Met Tyr Ser Lys Leu Arg Val
            405                 410                 415
Glu Lys Lys Asn Trp Val Glu Arg Asn Ser Tyr Ser Cys Ser Val Val
        420                 425                 430
His Glu Gly Leu His Asn His His Thr Thr Lys Ser Phe Ser Arg Thr
    435                 440                 445
Pro Gly Lys Arg Gly Arg Lys Arg Arg Ser Gly Ser Gly Ala Thr Asn
450                 455                 460
Phe Ser Leu Leu Lys Gln Ala Gly Asp Val Glu Glu Asn Pro Gly Pro
465                 470                 475                 480
Met Val Leu Gln Thr Gln Val Phe Ile Ser Leu Leu Leu Trp Ile Ser
                485                 490                 495
Gly Ala Tyr Gly Asp Ile Gln Met Thr Gln Ser Pro Ser Ser Leu Ser
            500                 505                 510
Ala Ser Val Gly Asp Arg Val Thr Ile Thr Cys Arg Ala Ser Gln Asp
        515                 520                 525
Val Ser Thr Ala Val Ala Trp Tyr Gln Gln Lys Pro Gly Lys Ala Pro
    530                 535                 540
Lys Leu Leu Ile Tyr Ser Ala Ser Phe Leu Tyr Ser Gly Val Pro Ser
545                 550                 555                 560
Arg Phe Ser Gly Ser Gly Ser Gly Thr Asp Phe Thr Leu Thr Ile Ser
                565                 570                 575
Ser Leu Gln Pro Glu Asp Phe Ala Thr Tyr Tyr Cys Gln Gln Ser Tyr
            580                 585                 590
Pro Ala Leu His Asp Phe Gly Gln Gly Thr Lys Val Glu Ile Lys Arg
        595                 600                 605
Ala Asp Ala Ala Pro Thr Val Ser Ile Phe Pro Pro Ser Ser Glu Gln
    610                 615                 620
Leu Thr Ser Gly Gly Ala Ser Val Val Cys Phe Leu Asn Asn Phe Tyr
625                 630                 635                 640
Pro Lys Asp Ile Asn Val Lys Trp Lys Ile Asp Gly Ser Glu Arg Gln
                645                 650                 655
Asn Gly Val Leu Asn Ser Trp Thr Asp Gln Asp Ser Lys Asp Ser Thr
            660                 665                 670
Tyr Ser Met Ser Ser Thr Leu Thr Leu Thr Lys Asp Glu Tyr Glu Arg
        675                 680                 685
His Asn Ser Tyr Thr Cys Glu Ala Thr His Lys Thr Ser Thr Ser Pro
    690                 695                 700
Ile Val Lys Ser Phe Asn Arg Asn Glu Cys
705                 710

<210> SEQ ID NO 2
<211> LENGTH: 2142
<212> TYPE: DNA
<213> ORGANISM: Artificial Sequence
<220> FEATURE:
<223> OTHER INFORMATION: Mouse PCSK9 DMAb

<400> SEQUENCE: 2
gaggtgcagc tggtggagtc cggcggaggc ctggtgcagc ctggaggctc tctgagactg      60
agctgcgctg cctccggctt caccttcagc agcaccgcta tccactgggt gcggcaggct     120
ccaggaaagg gcctggagtg ggtggctcgc atctctcctg ccaacggcaa cacaaactac     180
gctgacagcg tgaagggaag gttcaccatc tctgctgata agcaagaa caccgcctac     240 ctgcagatga actccctgag agctgaggac accgccgtgt actactgtgc caggtggatc     300

```
ggctctagag agctgtacat catggattac tggggacagg gcacactggt gaccgtgagc    360
agcgccaaga ccacagctcc atccgtgtac ccactggctc ccgtgtgcgg cgacaccaca    420
ggcagcagcg tgacactggg ctgtctggtg aagggatact ttcccgagcc tgtgaccctg    480
acatggaact ctggcagcct gagctccgga gtgcacacat tccctgccgt gctgcagagc    540
gacctgtaca ccctgtctag ctccgtgacc gtgacatcta gcacatggcc ttcccagtct    600
atcacctgca acgtggctca cccagcctcc tctacaaagg tggataagaa gatcgagcct    660
agaggcccaa ccatcaagcc ctgtccccct gcaagtgtc cagctccaaa cctgctggga    720
ggcccttccg tgttcatctt ccacccaag atcaaggacg tgctgatgat cagcctgtcc    780
cctatcgtga cctgcgtggt ggtggacgtg tccgaggacg atccagatgt gcagatctct    840
tggtttgtga acaacgtgga ggtgcacacc gctcagaccc agacacacag ggaggattac    900
aacagcacac tgagagtggt gtccgccctg cctatccagc accaggactg gatgagcggc    960
aaggagttca gtgcaaggt gaacaacaag gatctgcctg ctccaatcga ggaccatc      1020
tccaagccaa agggatctgt gagagcccct caggtgtacg tgctgcctcc acccgaggag    1080
gagatgacaa gaagcaggt gaccctgaca tgtatggtga ccgactttat gccagaggat    1140
atctacgtgg agtggacaaa caacggcaag accgagctga actacaagaa caccgagccc    1200
gtgctggaca gcgatggcag ctacttcatg tacagcaagc tgcgggtgga gaagaagaac    1260
tgggtggagc gcaactctta cagctgctcc gtggtgcacg agggcctgca caaccaccac    1320
accacaaagt cttttagccg gacccccaggc aagaggggaa ggaagaggag atccggatct    1380
ggcgctacaa acttctccct gctgaagcag gctggcgacg tggaggagaa cccaggacct    1440
atggtgctgc agacccaggt gttcatctct ctgctgctgt ggatcagcgg cgcctacgga    1500
gatatccaga tgacacagag cccaagctcc ctgagcgcct ccgtgggcga ccgggtgacc    1560
atcacatgta gggcttccca ggacgtgagc accgctgtgg cctggtacca gcagaagccc    1620
ggcaaggctc ctaagctgct gatctactct gccagcttcc tgtacagcgg agtgccctcc    1680
cggttttccg gatctggcag cggaaccgac ttcaccctga caatctctag cctgcagcca    1740
gaggattttg ctacatacta ctgccagcag tcttaccccg ccctgcacga cttcggacag    1800
ggaacaaagg tggagatcaa gcgcgctgat gctgccccta ccgtgagcat ctttcctcca    1860
tcctctgagc agctgacatc tggaggcgcc agcgtggtgt gcttcctgaa caacttttac    1920
ccaaaggaca tcaacgtgaa gtggaagatc gatggcagcg agaggcagaa cggagtgctg    1980
aactcctgga cagaccagga ttctaaggac agcacctact ccatgagctc caccctgaca    2040
ctgaccaagg atgagtacga gcggcacaac agctacacat gcgaggccac ccacaagaca    2100
tccacctctc ccatcgtgaa gtccttcaac cgcaacgagt gt                       2142
```

<210> SEQ ID NO 3
<211> LENGTH: 715
<212> TYPE: PRT
<213> ORGANISM: Artificial Sequence
<220> FEATURE:
<223> OTHER INFORMATION: Human PCSK9 DMAb

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

```
Ala Ile His Trp Val Arg Gln Ala Pro Gly Lys Gly Leu Glu Trp Val
         35                  40                  45
Ala Arg Ile Ser Pro Ala Asn Gly Asn Thr Asn Tyr Ala Asp Ser Val
 50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Trp Ile Gly Ser Arg Glu Leu Tyr Ile Met Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Lys Val Glu Pro Lys Ser Cys
    210                 215                 220
Asp Lys Thr His Thr Cys Pro Pro Cys Pro Ala Pro Glu Leu Leu Gly
225                 230                 235                 240
Gly Pro Ser Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
    290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
        435                 440                 445
Pro Gly Lys Arg Gly Arg Lys Arg Arg Ser Gly Ser Gly Ala Thr Asn
```

```
                450             455             460
Phe Ser Leu Leu Lys Gln Ala Gly Asp Val Glu Glu Asn Pro Gly Pro
465                 470                 475                 480

Met Val Leu Gln Thr Gln Val Phe Ile Ser Leu Leu Trp Ile Ser
                485                 490                 495

Gly Ala Tyr Gly Asp Asp Ile Gln Met Thr Gln Ser Pro Ser Ser Leu
                500                 505                 510

Ser Ala Ser Val Gly Asp Arg Val Thr Ile Thr Cys Arg Ala Ser Gln
                515                 520                 525

Asp Val Ser Thr Ala Val Ala Trp Tyr Gln Gln Lys Pro Gly Lys Ala
                530                 535                 540

Pro Lys Leu Leu Ile Tyr Ser Ala Ser Phe Leu Tyr Ser Gly Val Pro
545                 550                 555                 560

Ser Arg Phe Ser Gly Ser Gly Ser Gly Thr Asp Phe Thr Leu Thr Ile
                565                 570                 575

Ser Ser Leu Gln Pro Glu Asp Phe Ala Thr Tyr Tyr Cys Gln Gln Ser
                580                 585                 590

Tyr Pro Ala Leu His Asp Phe Gly Gln Gly Thr Lys Val Glu Ile Lys
                595                 600                 605

Arg Thr Val Ala Ala Pro Ser Val Phe Ile Phe Pro Pro Ser Asp Glu
                610                 615                 620

Gln Leu Lys Ser Gly Thr Ala Ser Val Val Cys Leu Leu Asn Asn Phe
625                 630                 635                 640

Tyr Pro Arg Glu Ala Lys Val Gln Trp Lys Val Asp Asn Ala Leu Gln
                645                 650                 655

Ser Gly Asn Ser Gln Glu Ser Val Thr Glu Gln Asp Ser Lys Asp Ser
                660                 665                 670

Thr Tyr Ser Leu Ser Ser Thr Leu Thr Leu Ser Lys Ala Asp Tyr Glu
                675                 680                 685

Lys His Lys Val Tyr Ala Cys Glu Val Thr His Gln Gly Leu Arg Ser
                690                 695                 700

Pro Val Thr Lys Ser Phe Asn Arg Gly Glu Cys
705                 710                 715

<210> SEQ ID NO 4
<211> LENGTH: 2145
<212> TYPE: DNA
<213> ORGANISM: Artificial Sequence
<220> FEATURE:
<223> OTHER INFORMATION: Human PCSK9 DMAb

<400> SEQUENCE: 4
gaggtgcagc tggtcgagag tggaggagga ctggtgcagc ccggcggcag cctgaggctg      60
tcctgcgccg cctctggctt cacctttagc tccacagcaa tccactgggt gaggcaggca     120
cctggcaagg gactggagtg ggtggccaga atctccccag ccaacggcaa taccaactac     180
gccgactctg tgaagggccg gtttacaatc agcgccgata cctccaagaa tacagcctat     240
ctgcagatga acagcctgag gcagaggac accgccgtgt actattgcgc caggtggatc     300
ggctccagag agctgtacat catggattat tggggccagg gcaccctggt gacagtgtct     360
agcgcctcta caagggacc tagcgtgttc ccactggcac cttcctctaa gtccacctct     420
ggcggcacag ccgccctggg ctgtctggtg aaggactact tcctgagcc agtgaccgtg     480 tcttggaata gcggcgccct gaccagcgga gtgcacacat tcccagccgt gctgcagagc     540
tccggactgt actccctgtc tagcgtggtg accgtgcctt cctctagcct gggcacccag     600
```

```
acatatatct gcaatgtgaa ccacaagcca agcaacacaa aggtggacaa gaaggtggag    660
cccaagtcct gtgataagac ccacacatgc cctccctgtc cagcacctga gctgctgggc    720
ggcccaagcg tgttcctgtt tccacccaag cctaaggaca ccctgatgat ctctaggacc    780
cctgaggtga catgcgtggt ggtggacgtg agccacgagg accccgaggt gaagtttaat    840
tggtacgtgg atggcgtgga ggtgcacaac gccaagacaa agccaaggga ggagcagtac    900
aactccacct atagagtggt gtctgtgctg acagtgctgc accaggactg gctgaatggc    960
aaggagtata agtgcaaggt gtccaacaag gccctgccag cccccatcga aagaccatc    1020
tctaaggcaa agggacagcc acgggagcca caggtgtaca cactgcctcc atctcgcgac   1080
gagctgacca agaatcaggt gagcctgaca tgtctggtga agggcttta tcccagcgat    1140
atcgcagtgg agtgggagtc caacggacag cctgagaaca attacaagac cacacccct    1200
gtgctggact ccgatggctc tttctttctg tattctaagc tgaccgtgga caagagccgg   1260
tggcagcagg gcaacgtgtt cagctgctcc gtgatgcacg aggccctgca caaccactac   1320
acccagaagt ctctgagcct gtcccctggc aagaggggaa ggaagaggag atctggcagc   1380
ggcgccacaa acttcagcct gctgaagcag gcaggcgatg tggaggagaa ccctggacca   1440
atggtgctgc agacccaggt gttcatcagc ctgctgctgt ggatctccgg cgcctacggc   1500
gacgatatcc agatgacaca gtccccttcc tctctgtccg cctctgtggg cgacagggtg   1560
accatcacat gtcgcgcctc tcaggatgtg agcaccgccg tggcctggta tcagcagaag   1620
cctggcaagg ccccaaagct gctgatctac agcgcctcct tcctgtattc cggcgtgcca   1680
tctcgctttt ctggcagcgg ctccggaacc gacttcaccc tgacaatcag ctccctgcag   1740
ccagaggatt ttgccacata ctattgccag cagagctacc ccgccctgca cgacttcgga   1800
cagggaacca aggtggagat caagaggaca gtggccgccc catccgtgtt catctttcca   1860
ccctctgatg agcagctgaa gagcggaacc gcatccgtgg tgtgcctgct gaacaatttc   1920
taccccagag aggccaaggt gcagtggaag gtggacaatg ccctgcagag cggcaactcc   1980
caggagtctg tgaccgagca ggacagcaag gattccacat attctctgtc tagcaccctg   2040
acactgtcca aggccgatta cgagaagcac aaggtgtatg cctgcgaggt cactcaccag   2100
gggctgcggt cacccgtcac caaatccttc aacaggggcg aatgc                   2145
```

<210> SEQ ID NO 5
<211> LENGTH: 733
<212> TYPE: PRT
<213> ORGANISM: Artificial Sequence
<220> FEATURE:
<223> OTHER INFORMATION: Mouse PCSK9 DMAb + Leader Sequence

<400> SEQUENCE: 5

Met Asp Trp Thr Trp Arg Ile Leu Phe Leu Val Ala Ala Thr Gly
1               5                   10                  15

Thr His Ala Glu Val Gln Leu Val Glu Ser Gly Gly Gly Leu Val Gln
                20                  25                  30

Pro Gly Gly Ser Leu Arg Leu Ser Cys Ala Ala Ser Gly Phe Thr Phe
        35                  40                  45

Ser Ser Thr Ala Ile His Trp Val Arg Gln Ala Pro Gly Lys Gly Leu
    50                  55                  60

Glu Trp Val Ala Arg Ile Ser Pro Ala Asn Gly Asn Thr Asn Tyr Ala
65                  70                  75                  80

Asp Ser Val Lys Gly Arg Phe Thr Ile Ser Ala Asp Thr Ser Lys Asn

-continued

```
                85                  90                  95
Thr Ala Tyr Leu Gln Met Asn Ser Leu Arg Ala Glu Asp Thr Ala Val
            100                 105                 110
Tyr Tyr Cys Ala Arg Trp Ile Gly Ser Arg Glu Leu Tyr Ile Met Asp
            115                 120                 125
Tyr Trp Gly Gln Gly Thr Leu Val Thr Val Ser Ser Ala Lys Thr Thr
    130                 135                 140
Ala Pro Ser Val Tyr Pro Leu Ala Pro Val Cys Gly Asp Thr Thr Gly
145                 150                 155                 160
Ser Ser Val Thr Leu Gly Cys Leu Val Lys Gly Tyr Phe Pro Glu Pro
                165                 170                 175
Val Thr Leu Thr Trp Asn Ser Gly Ser Leu Ser Ser Gly Val His Thr
                180                 185                 190
Phe Pro Ala Val Leu Gln Ser Asp Leu Tyr Thr Leu Ser Ser Ser Val
            195                 200                 205
Thr Val Thr Ser Ser Thr Trp Pro Ser Gln Ser Ile Thr Cys Asn Val
    210                 215                 220
Ala His Pro Ala Ser Ser Thr Lys Val Asp Lys Lys Ile Glu Pro Arg
225                 230                 235                 240
Gly Pro Thr Ile Lys Pro Cys Pro Pro Cys Lys Cys Pro Ala Pro Asn
                245                 250                 255
Leu Leu Gly Gly Pro Ser Val Phe Ile Phe Pro Pro Lys Ile Lys Asp
                260                 265                 270
Val Leu Met Ile Ser Leu Ser Pro Ile Val Thr Cys Val Val Val Asp
            275                 280                 285
Val Ser Glu Asp Asp Pro Asp Val Gln Ile Ser Trp Phe Val Asn Asn
            290                 295                 300
Val Glu Val His Thr Ala Gln Thr Gln Thr His Arg Glu Asp Tyr Asn
305                 310                 315                 320
Ser Thr Leu Arg Val Val Ser Ala Leu Pro Ile Gln His Gln Asp Trp
                325                 330                 335
Met Ser Gly Lys Glu Phe Lys Cys Lys Val Asn Asn Lys Asp Leu Pro
                340                 345                 350
Ala Pro Ile Glu Arg Thr Ile Ser Lys Pro Lys Gly Ser Val Arg Ala
            355                 360                 365
Pro Gln Val Tyr Val Leu Pro Pro Glu Glu Glu Met Thr Lys Lys
            370                 375                 380
Gln Val Thr Leu Thr Cys Met Val Thr Asp Phe Met Pro Glu Asp Ile
385                 390                 395                 400
Tyr Val Glu Trp Thr Asn Asn Gly Lys Thr Glu Leu Asn Tyr Lys Asn
                405                 410                 415
Thr Glu Pro Val Leu Asp Ser Asp Gly Ser Tyr Phe Met Tyr Ser Lys
                420                 425                 430
Leu Arg Val Glu Lys Lys Asn Trp Val Glu Arg Asn Ser Tyr Ser Cys
            435                 440                 445
Ser Val Val His Glu Gly Leu His Asn His His Thr Thr Lys Ser Phe
    450                 455                 460
Ser Arg Thr Pro Gly Lys Arg Gly Arg Lys Arg Arg Ser Gly Ser Gly
465                 470                 475                 480
Ala Thr Asn Phe Ser Leu Leu Lys Gln Ala Gly Asp Val Glu Glu Asn
                485                 490                 495
Pro Gly Pro Met Val Leu Gln Thr Gln Val Phe Ile Ser Leu Leu Leu
            500                 505                 510
```

```
Trp Ile Ser Gly Ala Tyr Gly Asp Ile Gln Met Thr Gln Ser Pro Ser
        515                 520                 525

Ser Leu Ser Ala Ser Val Gly Asp Arg Val Thr Ile Thr Cys Arg Ala
    530                 535                 540

Ser Gln Asp Val Ser Thr Ala Val Ala Trp Tyr Gln Gln Lys Pro Gly
545                 550                 555                 560

Lys Ala Pro Lys Leu Leu Ile Tyr Ser Ala Ser Phe Leu Tyr Ser Gly
                565                 570                 575

Val Pro Ser Arg Phe Ser Gly Ser Gly Ser Gly Thr Asp Phe Thr Leu
                580                 585                 590

Thr Ile Ser Ser Leu Gln Pro Glu Asp Phe Ala Thr Tyr Tyr Cys Gln
            595                 600                 605

Gln Ser Tyr Pro Ala Leu His Asp Phe Gly Gln Gly Thr Lys Val Glu
        610                 615                 620

Ile Lys Arg Ala Asp Ala Ala Pro Thr Val Ser Ile Phe Pro Pro Ser
625                 630                 635                 640

Ser Glu Gln Leu Thr Ser Gly Gly Ala Ser Val Val Cys Phe Leu Asn
                645                 650                 655

Asn Phe Tyr Pro Lys Asp Ile Asn Val Lys Trp Lys Ile Asp Gly Ser
                660                 665                 670

Glu Arg Gln Asn Gly Val Leu Asn Ser Trp Thr Asp Gln Asp Ser Lys
            675                 680                 685

Asp Ser Thr Tyr Ser Met Ser Ser Thr Leu Thr Leu Thr Lys Asp Glu
        690                 695                 700

Tyr Glu Arg His Asn Ser Tyr Thr Cys Glu Ala Thr His Lys Thr Ser
705                 710                 715                 720

Thr Ser Pro Ile Val Lys Ser Phe Asn Arg Asn Glu Cys
                725                 730

<210> SEQ ID NO 6
<211> LENGTH: 2199
<212> TYPE: DNA
<213> ORGANISM: Artificial Sequence
<220> FEATURE:
<223> OTHER INFORMATION: Mouse PCSK9 DMAb + Leader Sequence

<400> SEQUENCE: 6
atggactgga cctggagaat cctgttcctg gtggctgctg ctaccggaac acacgctgag      60
gtgcagctgg tggagtccgg cggaggcctg gtgcagcctg gaggctctct gagactgagc     120
tgcgctgcct ccggcttcac cttcagcagc accgctatcc actgggtgcg gcaggctcca     180
ggaaagggcc tggagtgggt ggctcgcatc tctcctgcca acggcaacac aaactacgct     240
gacagcgtga aggaaggtt caccatctct gctgatacaa gcaagaacac cgcctacctg     300
cagatgaact ccctgagagc tgaggacacc gccgtgtact actgtgccag gtggatcggc     360
tctagagagc tgtacatcat ggattactgg ggacagggca ctggtgac cgtgagcagc      420 gccaagacca cagctccatc cgtgtaccca ctggctcccg tgtgcggcga caccacaggc     480
agcagcgtga cactgggctg tctggtgaag ggatactttc ccgagcctgt gaccctgaca     540
tggaactctg gcagcctgag ctccggagtg cacacattcc tgccgtgct gcagagcgac     600 ctgtacaccc tgtctagctc cgtgaccgtg acatctagca catggcttc ccagtctatc     660 acctgcaacg tggctcaccc agcctcctct acaaaggtgg ataagaagat cgagcctaga     720
ggcccaacca tcaagccctg tccccttgc aagtgtccag ctccaaacct gctgggaggc     780
```

```
cctteegtgt tcatctttcc acccaagatc aaggacgtgc tgatgatcag cctgtcccct    840
atcgtgacct gcgtggtggt ggacgtgtcc gaggacgatc agatgtgcag gatctcttgg    900
tttgtgaaca acgtggaggt gcacaccgct cagacccaga cacacaggga ggattacaac    960
agcacactga gagtggtgtc cgccctgcct atccagcacc aggactggat gagcggcaag   1020
gagttcaagt gcaaggtgaa caacaaggat ctgcctgctc aatcgagag gaccatctcc    1080
aagccaaagg gatctgtgag agcccctcag gtgtacgtgc tgcctccacc cgaggaggag   1140
atgacaaaga agcaggtgac cctgacatgt atggtgaccg actttatgcc agaggatatc   1200
tacgtggagt ggacaaacaa cggcaagacc gagctgaact acaagaacac cgagcccgtg   1260
ctggacagcg atggcagcta cttcatgtac agcaagctgc gggtggagaa gaagaactgg   1320
gtggagcgca actcttacag ctgctccgtg gtgcacgagg cctgcacaa ccaccacacc     1380
acaaagtctt ttagccggac cccaggcaag aggggaagga gaggagatc cggatctggc    1440
gctacaaact tctccctgct gaagcaggct ggcgacgtgg aggagaaccc aggacctatg   1500
gtgctgcaga cccaggtgtt catctctctg ctgctgtgga tcagcggcgc ctacggagat   1560
atccagatga cacagagccc aagctccctg agcgcctccg tgggcgaccg ggtgaccatc   1620
acatgtaggg cttcccagga cgtgagcacc gctgtggcct ggtaccagca gaagcccggc   1680
aaggctccta agctgctgat ctactctgcc agcttcctgt acagcggagt gccctcccgg   1740
ttttccggat ctggcagcgg aaccgacttc accctgacaa tctctagcct gcagccagag   1800
gattttgcta catactactg ccagcagtct taccccgccc tgcacgactt cggacaggga   1860
acaaaggtgg agatcaagcg cgctgatgct gcccctaccg tgagcatctt tcctccatcc   1920
tctgagcagc tgacatctgg aggcgccagc gtggtgtgct tcctgaacaa cttttaccca   1980
aaggacatca cgtgaagtg gaagatcgat ggcagcgaga ggcagaacgg agtgctgaac    2040
tcctggacag accaggattc taaggacagc acctactcca tgagctccac cctgacactg   2100
accaaggatg agtacgagcg gcacaacagc tacacatgcg aggccaccca caagacatcc   2160
acctctccca tcgtgaagtc cttcaaccgc aacgagtgt                          2199
```

<210> SEQ ID NO 7
<211> LENGTH: 734
<212> TYPE: PRT
<213> ORGANISM: Artificial Sequence
<220> FEATURE:
<223> OTHER INFORMATION: Human PCSK9 DMAb + Leader Sequence

<400> SEQUENCE: 7

```
Met Asp Trp Thr Trp Arg Ile Leu Phe Leu Val Ala Ala Ala Thr Gly
1               5                   10                  15

Thr His Ala Glu Val Gln Leu Val Glu Ser Gly Gly Gly Leu Val Gln
            20                  25                  30

Pro Gly Ser Leu Arg Leu Ser Cys Ala Ala Ser Gly Phe Thr Phe
        35                  40                  45

Ser Ser Thr Ala Ile His Trp Val Arg Gln Ala Pro Gly Lys Gly Leu
    50                  55                  60

Glu Trp Val Ala Arg Ile Ser Pro Ala Asn Gly Asn Thr Asn Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
                100                 105                 110
```

-continued

```
Tyr Tyr Cys Ala Arg Trp Ile Gly Ser Arg Glu Leu Tyr Ile Met Asp
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
    195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
    275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
    355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
    435                 440                 445

Ser Val Met His Glu Ala Leu His Asn His Tyr Thr Gln Lys Ser Leu
450                 455                 460

Ser Leu Ser Pro Gly Lys Arg Gly Arg Lys Arg Arg Ser Gly Ser Gly
465                 470                 475                 480

Ala Thr Asn Phe Ser Leu Leu Lys Gln Ala Gly Asp Val Glu Glu Asn
                485                 490                 495

Pro Gly Pro Met Val Leu Gln Thr Gln Val Phe Ile Ser Leu Leu Leu
            500                 505                 510

Trp Ile Ser Gly Ala Tyr Gly Asp Asp Ile Gln Met Thr Gln Ser Pro
    515                 520                 525

Ser Ser Leu Ser Ala Ser Val Gly Asp Arg Val Thr Ile Thr Cys Arg
```

```
                530             535             540
Ala Ser Gln Asp Val Ser Thr Ala Val Ala Trp Tyr Gln Gln Lys Pro
545                 550                 555                 560

Gly Lys Ala Pro Lys Leu Leu Ile Tyr Ser Ala Ser Phe Leu Tyr Ser
                565                 570                 575

Gly Val Pro Ser Arg Phe Ser Gly Ser Gly Ser Gly Thr Asp Phe Thr
                580                 585                 590

Leu Thr Ile Ser Ser Leu Gln Pro Glu Asp Phe Ala Thr Tyr Tyr Cys
                595                 600                 605

Gln Gln Ser Tyr Pro Ala Leu His Asp Phe Gly Gln Gly Thr Lys Val
                610                 615                 620

Glu Ile Lys Arg Thr Val Ala Ala Pro Ser Val Phe Ile Phe Pro Pro
625                 630                 635                 640

Ser Asp Glu Gln Leu Lys Ser Gly Thr Ala Ser Val Val Cys Leu Leu
                645                 650                 655

Asn Asn Phe Tyr Pro Arg Glu Ala Lys Val Gln Trp Lys Val Asp Asn
                660                 665                 670

Ala Leu Gln Ser Gly Asn Ser Gln Glu Ser Val Thr Glu Gln Asp Ser
                675                 680                 685

Lys Asp Ser Thr Tyr Ser Leu Ser Ser Thr Leu Thr Leu Ser Lys Ala
                690                 695                 700

Asp Tyr Glu Lys His Lys Val Tyr Ala Cys Glu Val Thr His Gln Gly
705                 710                 715                 720

Leu Arg Ser Pro Val Thr Lys Ser Phe Asn Arg Gly Glu Cys
                725                 730

<210> SEQ ID NO 8
<211> LENGTH: 2202
<212> TYPE: DNA
<213> ORGANISM: Artificial Sequence
<220> FEATURE:
<223> OTHER INFORMATION: Human PCSK9 DMAb + Leader Sequence

<400> SEQUENCE: 8
atggactgga cttggagaat tctgtttctg gtcgccgccg ctaccgggac tcacgccgag      60
gtgcagctgg tcgagagtgg aggaggactg gtgcagcccg gcggcagcct gaggctgtcc    120
tgcgccgcct ctggcttcac ctttagctcc acagcaatcc actgggtgag gcaggcacct    180
ggcaagggac tggagtgggt ggccagaatc tccccagcca acggcaatac caactacgcc    240
gactctgtga agggccggtt tacaatcagc gccgatacct ccaagaatac agcctatctg    300
cagatgaaca gcctgagggc agaggacacc gccgtgtact attgcgccag gtggatcggc    360
tccagagagc tgtacatcat ggattattgg ggccagggca ccctggtgac agtgtctagc    420
gcctctacaa agggacctag cgtgttccca ctggcaccct cctctaagtc cacctctggc    480
ggcacagccg ccctgggctg tctggtgaag gactactttc ctgagccagt gaccgtgtct    540
tggaatagcg gcgccctgac cagcggagtg cacacattcc cagccgtgct gcagagctcc    600
ggactgtact ccctgtctag cgtggtgacc gtgccttcct ctagcctggg cacccagaca    660
tatatctgca atgtgaacca caagccaagc aacacaaagg tggacaagaa ggtgagccc     720 aagtcctgtg ataagaccca cacatgccct ccctgtccag cacctgagct gctgggcggc    780
ccaagcgtgt tcctgtttcc acccaagcct aaggacaccc tgatgatctc taggacccct    840
gaggtgacat gcgtggtggt ggacgtgagc cacgaggacc ccgaggtgaa gtttaattgg    900
tacgtggatg gcgtggaggt gcacaacgcc aagacaaagc caagggagga gcagtacaac    960
```

```
tccacctata gagtggtgtc tgtgctgaca gtgctgcacc aggactggct gaatggcaag    1020
gagtataagt gcaaggtgtc caacaaggcc ctgccagccc ccatcgagaa gaccatctct    1080
aaggcaaagg gacagccacg ggagccacag gtgtacacac tgcctccatc tcgcgacgag    1140
ctgaccaaga atcaggtgag cctgacatgt ctggtgaagg gcttttatcc cagcgatatc    1200
gcagtggagt gggagtccaa cggacagcct gagaacaatt acaagaccac accccctgtg    1260
ctggactccg atggctcttt ctttctgtat tctaagctga ccgtggacaa gagccggtgg    1320
cagcagggca acgtgttcag ctgctccgtg atgcacgagg ccctgcacaa ccactacacc    1380
cagaagtctc tgagcctgtc ccctggcaag aggggaagga agaggagatc tggcagcggc    1440
gccacaaact tcagcctgct gaagcaggca ggcgatgtgg aggagaaccc tggaccaatg    1500
gtgctgcaga cccaggtgtt catcagcctg ctgctgtgga tctccggcgc ctacggcgac    1560
gatatccaga tgacacagtc cccttcctct ctgtccgcct ctgtgggcga cagggtgacc    1620
atcacatgtc gcgcctctca ggatgtgagc accgccgtgg cctggtatca gcagaagcct    1680
ggcaaggccc caaagctgct gatctacagc gcctccttcc tgtattccgg cgtgccatct    1740
cgcttttctg gcagcggctc cggaaccgac ttcaccctga caatcagctc cctgcagcca    1800
gaggattttg ccacatacta ttgccagcag agctaccccg ccctgcacga cttcggacag    1860
ggaaccaagg tggagatcaa gaggacagtg gccgcccat ccgtgttcat ctttccaccc     1920
tctgatgagc agctgaagag cggaaccgca tccgtggtgt gcctgctgaa caatttctac    1980
cccagagagg ccaaggtgca gtggaaggtg gacaatgccc tgcagagcgg caactcccag    2040
gagtctgtga ccgagcagga cagcaaggat tccacatatt ctctgtctag caccctgaca    2100
ctgtccaagg ccgattacga gaagcacaag gtgtatgcct gcgaggtcac tcaccagggg    2160
ctgcggtcac ccgtcaccaa atccttcaac aggggcgaat gc                       2202
```

NUCLEIC ACID MONOCLONAL ANTIBODIES TARGETING PCSK9 AND METHODS OF USE

CROSS-REFERENCE TO RELATED APPLICATIONS

This application is a U.S. national phase application filed under 35 U.S.C. § 371 claiming priority to International Patent Application No. PCT/US19/15972, filed Jan. 31, 2019, which is entitled to priority under 35 U.S.C. § 119(e) to U.S. Provisional Patent Application No. 62/624,297, filed Jan. 31, 2018, the contents of each of which are incorporated by reference herein in their entireties.

TECHNICAL FIELD

The present invention relates to a composition comprising a recombinant nucleic acid sequence for generating one or more synthetic antibodies, including antibodies targeting one LDL-C modulators (e.g., PCSK9 and functional fragments thereof), in vivo, and a method of preventing and/or treating cardiovascular diseases and disorders and other conditions in a subject by administering said composition.

REFERENCE TO SEQUENCE LISTING ELECTRONICALLY

The instant application contains a Sequence Listing which has been submitted electronically in computer readable format and is hereby incorporated by reference in its entirety. The Sequence Listing is written in the accompanying text file titled: "206193-0004-00US_Sequence_Listing_ST25.TXT"; created on Jul. 28, 2020, and 37,409 bytes in size.

BACKGROUND

Cardiovascular disease is the leading cause of death worldwide with more approximately 600,00 deaths per year in the United States and 17.3 million deaths per year worldwide. Elevated LDL-C is one of the major contributors to cardiovascular heart disease and atherosclerosis. Statins have been found to be very effective in lowering LDL-C levels, however serious adverse side-effects have been reported, resulting in some cases to discontinuation of the treatment. One of the most promising alternatives to statins are proprotein convertase subtilisin-like kexin type 9 (PCSK9) inhibitors that reduce LDL-C by increasing their hepatic clearance via the LDL receptor. Protein-based monoclonal antibodies (mAbs) against PCSK9 have shown great efficacy in LDL-C reduction. Unfortunately, the high cost of protein-based mAbs is one of the major constraints in clinical management of at-risk cardiovascular patients.

Thus, there is a need in the art for improved, cost-effective compositions and methods for treatment cardiovascular diseases and disorders of patients deemed statin-intolerant.

SUMMARY

The present invention is directed to compositions for generating one or more anti-PCSK9 antibodies or fragments thereof in a subject. In one embodiment, the composition comprises one or more nucleic acid molecules encoding one or more anti-PCSK9 antibodies or fragments thereof.

In one embodiment, the nucleic acid molecule comprises a nucleotide sequence encoding a cleavage domain. In one embodiment, the nucleic acid molecule comprises a nucleotide sequence encoding a polypeptide comprising a constant heavy chain region and a polypeptide comprising a constant light chain region. In one embodiment, the nucleic acid molecule comprises a nucleotide sequence encoding a polypeptide comprising a variable heavy chain region; a constant heavy chain region; a cleavage domain; a variable light chain region; and a constant light chain region.

In one embodiment, the nucleotide sequence encodes a leader sequence. In one embodiment, the nucleotide sequence encodes an amino acid sequence having at least about 90% identity over the entire length of at least one amino acid sequence selected from the group of SEQ ID NOs: 1, 3, 5 and 7.

In one embodiment, the nucleotide sequence comprises a nucleotide sequence having at least about 80% identity over the entire length of at least one nucleotide sequence selected from the group of SEQ ID NOs: 2, 4, 6 and 8.

In one embodiment, the one or more nucleic acid molecules are engineered to be in an expression vector.

In one embodiment, the composition comprises a pharmaceutically acceptable excipient.

The present invention provides a method of treating a disease in a subject. In one embodiment, the method comprises administering to the subject a composition of the invention. In one embodiment, the disease is cardiovascular disease or hypercholesterolemia. In one embodiment, administering the composition comprises an electroporating step.

The present invention provides a method for decreasing an LDL-C in a subject in need thereof. In one embodiment, the method comprises administering to the subject a composition of the invention. In one embodiment, administering the composition comprises an electroporating step.

BRIEF DESCRIPTION OF THE DRAWINGS

FIG. 1A and FIG. 1B, depicts an illustration of DMAb approach. FIG. 1A depicts the anti-PCSK9 DMAbs and mechanism of action. An in vivo electroporation device is used for intracellular delivery of anti-PCSK9 DMAb plasmids. Next, there is intramuscular expression of DNA-encoded anti-PCSK9 mAbs and their subsequent release into the circulation. Next, anti-PCSK9 DMAbs migrate to the liver where they bind and inhibit PCSK9. The anti-PCSK9 DMAb mechanism of action: LDL binding to LDLR results in uptake and degradation of LDL and recycling of LDLR. Next, PCSK9 binds LDLR, resulting in LDLR degradation. Finally, anti-PCSK9 DMAb inhibits PCSK9, allowing for increased LDLR recycling and display on the cell surface. FIG. 1A depicts a schematic of the anti-PCSK9 DMAb bicistronic plasmid consisting of antibody heavy- and light-chain sequences separated by furin and P2A cleavage sites.

FIG. 2A through FIG. 2C, depicts the in vitro Evaluation of MdaPCSK9. FIG. 2A depicts the in vitro expression of MdaPCSK9 compared to empty backbone pVax-1 plasmid in HEK293 cells. Supernatants were harvested at 24, 48, and 72 hours post-transfection and analyzed by quantitative ELISA. FIG. 2B depicts binding western blot analysis of MdaPCSK9 from cellular supernatants. Binding of MdaPCSK9 obtained from HEK293T transfected cells was evaluated against recombinant mouse and human PCSK9 proteins. Membranes were stained with supernatant from MdaPCSK9- or pVax-1-transfected cells at 72 hours post-transfection. FIG. 2C depicts immunofluorescence staining of mouse Hepa1-6 cells transfected with MdaPCSK9 plasmids. Cells were fixed 48 hours after transfection. Cells were stained with anti-mouse IgG-FITC and DAPI nuclear stain. pVax-1-transfected cells were used as a negative control.

FIG. 3A through FIG. 3C, depicts the in vivo expression and kinetics of MdaPCSK9. FIG. 3A depicts quantitative ELISA analysis for MdaPCSK9 following a single intramuscular injection of DMAb plasmids in B6.Cg-foxn1nu/J nude mice. FIG. 3B depicts quantitative ELISA analysis for MdaPCSK9 following a single intramuscular injection of DMAb plasmids in C57BL/6J wild-type mice. FIG. 3C depicts sequential administrations of MdaPCSK9 by intramuscular injection in C57BL/6J wild-type mice at days 0, 21, and 42. Quantitative ELISA analysis was performed for MdaPCSK9 at the indicated time points. Plates were coated with recombinant mouse PCSK9 protein, followed by incubation with anti-mouse IgG-HRP for the detection of MdaPCSK9. Values represent mean expression in each group (n=5)±SEM.

FIG. 4A through FIG. 4F, depicts the evaluation of binding and functional activity of MdaPCSK9. FIG. 4A depicts western analysis of liver LDLR expression. Livers of control- and DMAb-treated C57B/6J wild-type mice were harvested at day 5 post-treatment. Levels of LDLR expression in tissue lysates were evaluated by staining for anti-mouse LDLR antibody. FIG. 4B depicts quantitative ELISA for MdaPCSK9 was performed on liver lysates at day 5 post-treatment. FIG. 4C depicts binding western blot analysis of anti-PCSK9 DMAbs from mouse sera. Anti-PCSK9 DMAbs obtained from mouse sera at 5 days post-treatment were evaluated for binding against recombinant mouse and human PCSK9 proteins.

FIGS. 4D through 4F depict flow cytometry analysis performed for LDLR expression in Huh7 cells. Human hepatoma Huh7 cells were treated with pVax-1 control DNA or MdaPCSK9 and harvested at 72 hours post-treatment. The level of LDLR expression was evaluated by flow cytometry by staining with anti-LDL receptor antibody (ab52818), followed by anti-rabbit IgG-FITC (sc-2012). FIG. 4D depicts a histogram of Huh7 cells treated with pVax-1 or MdaPCSK9. FIG. 4E depicts a dot plot of Huh7 cells treated with pVax-1 or MdaPCSK9. FIG. 4F depicts a mean fluorescence intensity (MFI) of Huh7 cells treated with pVax-1 or MdaPCSK9.

FIG. 5A through FIG. 5F, depicts in vivo lipid panel analysis of MdaPCSK9. Lipid panel analyses were carried out on mice sera using the VITROS 350 Clinical Chemistry Analyzer. Percent changes were calculated for each day relative to control pVax-1-treated mice. Statistical differences are indicated relative to day 0 of treatment. Data are expressed as ±SEM (n=5). Statistical differences were measured using two-way ANOVA tests ($*p<0.05$, $p<0.01$, and $*p<0.001$; n.s., not significant). FIG. 5A depicts the non-HDL-C of B6.Cg-foxn1nu/J nude mice which were bled at the indicated time points following a single intramuscular administration of 300 μg MdaPCSK9 plasmid. FIG. 5B depicts the total cholesterol of B6.Cg-foxn1nu/J nude mice which were bled at the indicated time points following a single intramuscular administration of 300 μg MdaPCSK9 plasmid. FIG. 5C depicts the total cholesterol of C57B/6J wild-type mice that were bled at the indicated time points following a single intramuscular administration of 300 μg MdaPCSK9 plasmid. FIG. 5D depicts the non-HDL-C of C57B/6J wild-type mice that were bled at the indicated time points following a single intramuscular administration of 300 μg MdaPCSK9 plasmid. FIG. 5E depicts the total cholesterol of C57B/6J wild-type mice that were sequentially administered 100 μg MdaPCSK9 plasmid by intramuscular injection. FIG. 5F depicts the non-HDL-C of C57B/6J wild-type mice that were sequentially administered 100 μg MdaPCSK9 plasmid by intramuscular injection.

FIG. 6A through FIG. 6D, depicts in vivo expression and kinetics of HdaPCSK9. FIGS. 6A and 6B depicts quantitative ELISA analysis for MdaPCSK9 following single intramuscular injection of DMAb plasmids. Quantitative ELISAs were performed for anti-hPCSK9 DMAb at the indicated time points. Plates were coated with anti-human Fc antibody, followed by incubation with anti-human IgG-HRP antibody for the detection of HdaPCSK9. Values represent mean expression in each group (n=5) ±SEM. FIG. 6A depicts quantitative ELISA analysis for MdaPCSK9 following single intramuscular injection of DMAb plasmids in B6.Cg-foxn1nu/J nude mice. FIG. 6B depicts quantitative ELISA analysis for MdaPCSK9 following single intramuscular injection of DMAb plasmids in C57BL/6J wild-type mice. FIG. 6C depicts binding western blot analysis of HdaPCSK9 from mouse sera. Anti-PCSK9 DMAbs obtained from mouse sera at 5 days post-treatment were evaluated for binding against recombinant mouse and human PCSK9 proteins. FIG. 6D depicts histology and immunohistochemistry of HdaPCSK9 in mouse muscle (magnification, 20×; scale bars, 100 μm). Immunohistochemistry of PCSK9 using anti-human IgG-HRP for mouse muscle sections at day 5 in C57BL/6J wild-type is shown. Insets show 30% magnification of the images. Prominent browning is detected in HdaPCSK9-treated muscle. H&E-stained sections of treated muscle show no observable tissue damage. The images were taken from the muscle mid-section, away from the needle tract area.

FIG. 7A through FIG. 7C, depicts in vitro evaluation of HdaPCSK9. FIG. 7A depicts in vitro expression of HdaPCSK9 compared to empty backbone pVax-1 plasmid in HEK293 cells. Supernatants were harvested at 24 hours, 48 hours, and 72 hours post-transfection, and analyzed by quantitative ELISA. FIG. 7B depicts binding western blot analysis of HdaPCSK9 from cellular supernatants. Binding of HdaPCSK9 obtained from HEK293T transfected cells was evaluated against recombinant mouse and human PCSK9 proteins. Membranes were stained with supernatant from HdaPCSK9 or pVax-1 transfected cells at 72 hours post-transfection. FIG. 7C depicts immunofluorescence staining of mouse Hepa1-6 cells transfected with HdaPCSK9 plasmids. Cells were fixed 48 hours after transfection. Cells were stained with anti-human IgG-FITC and DAPI nuclear stain. pVax-1 transfected cells were used as a negative control.

FIG. 8A through FIG. 8D, depicts in vivo lipid panel analysis of HdaPCSK9. Lipid panel (non-HDL-C and total cholesterol) analysis was carried out on mouse sera using a VITROS 350 Clinical Chemistry Analyzer. Percent changes were calculated for each day relative to control pVax-1 treated mice. Statistical differences are indicated relative to day 0 of treatment. Data are expressed as ±SEM (n=5). Statistical differences were measured using two-way ANOVA tests ($*p<0.05$, $**p<0.001$, n.s.=not significant). FIG. 8A depicts non-HDL-C of B6.Cg-foxn1nu/J nude mice that were bled at indicated timepoints following a single intramuscular administration of 300 μg HdaPCSK9 plasmid. FIG. 8B total cholesterol of B6.Cg-foxn1nu/J nude mice that were bled at indicated timepoints following a single intramuscular administration of 300 μg HdaPCSK9 plasmid. FIG. 8C depicts non-HDL-C of C57BL/6J wild-type mice that were bled at indicated timepoints following a single intramuscular administration of 300 µg HdaPCSK9 plasmid. FIG. 8D total cholesterol of C57BL/6J wild-type mice that were bled at indicated timepoints following a single intramuscular administration of 300 µg HdaPCSK9 plasmid.

DETAILED DESCRIPTION

Figure 1:
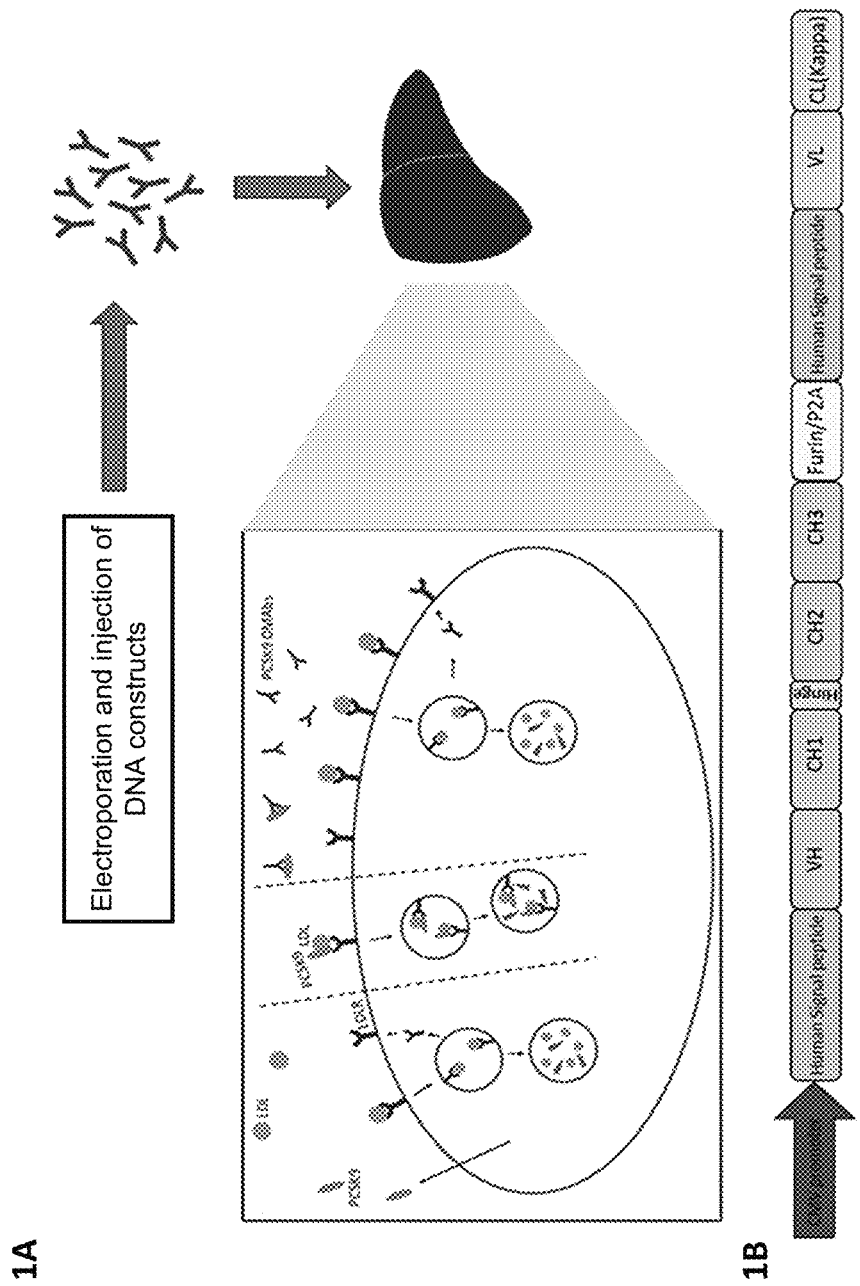
FIG. 1, comprising

The present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody.

In particular, the heavy chain and light chain polypeptides expressed from the recombinant nucleic acid sequences can assemble into the synthetic antibody. The heavy chain polypeptide and the light chain polypeptide can interact with one another such that assembly results in the synthetic antibody being capable of binding the antigen, being more immunogenic as compared to an antibody not assembled as described herein, and being capable of eliciting or inducing an immune response against the antigen.

Additionally, these synthetic antibodies are generated more rapidly in the subject than antibodies that are produced in response to antigen induced immune response. The synthetic antibodies are able to effectively bind and neutralize a range of antigens. The synthetic antibodies are also able to effectively protect against and/or promote survival of disease. In one aspect, the present invention relates to a composition that can be used to treat or prevent a cardiovascular disease or disorder or hypercholesterolemia, by administering a PCSK9 inhibitor, such as an engineered or synthetic antibody directed to PCSK9 (e.g., engineered MAb in the form of synthetic DNA plasmids; "DMAb").

With respect to engineered MAb in the form of synthetic DNA plasmids, the present invention relates to compositions comprising a recombinant nucleic acid sequence encoding an antibody, a fragment thereof, a variant thereof, or a combination thereof. The composition can be administered to a subject in need thereof to facilitate in vivo expression and formation of a synthetic antibody. In one embodiment, the nucleotide sequence comprises one or more nucleotide sequences described herein. In one embodiment, the nucleotide sequence comprises sequence encoding the polypeptide sequence of SEQ ID NOs: 1, 3, 5, or 7, or a variant thereof or a fragment thereof. In one embodiment, the nucleotide sequence comprises an RNA sequence transcribed from a DNA sequence described herein. For example, in one embodiment, the nucleotide sequence comprises an RNA sequence transcribed by a DNA sequence encoding the polypeptide sequence of SEQ ID NOs: 1, 3, 5, or 7, or a variant thereof or a fragment thereof.

In one embodiment, the nucleotide sequence encodes an amino acid sequence having at least about 80%, at least about 85%, at least about 90%, or at least about 95% identity over the entire length of the amino acid sequence to an amino acid sequence selected from the group SEQ ID NOs: 1, 3, 5, and 7. In one embodiment, the nucleotide sequence encodes a fragment of an amino acid sequence having at least about 80%, at least about 85%, at least about 90%, or at least about 95% identity over the entire length of the amino acid sequence to an amino acid sequence selected from the group SEQ ID NOs: 1, 3, 5, and 7.

In one embodiment, the nucleotide sequence has at least about 80%, at least about 85%, at least about 90%, or at least about 95% identity over the entire length of the nucleotide sequence to one or more nucleotide sequences encoding one or more of SEQ ID NOs: 1, 3, 5, and 7. In one embodiment, the nucleotide sequence is a fragment of a nucleotide sequence that has at least about 80%, at least about 85%, at least about 90%, or at least about 95% identity over the entire length of the nucleotide sequence to one or more nucleotide sequences encoding one or more of SEQ ID NOs: 1, 3, 5, and 7.

In one embodiment, nucleotide sequence has at least about 80% identity over the entire length of at least one nucleotide sequence selected from the group of SEQ ID NOs: 2, 4, 6 and 8.

The composition of the present invention can decrease the low-density lipoprotein cholesterol (LDL-C) levels in the subject, as compared to a subject not receiving the PCSK9 DMAb. The composition of the present invention can be administered to subjects who have adverse reactions to statins and therefore are deemed statin-intolerant.

The compositions provided herein can also include a pharmaceutically acceptable excipient.

Aspects of the invention also include methods for increasing an immune response in a subject in need thereof by administering any of the compositions provided herein to the subject. The methods of increasing an immune response can also include an electroporating step.

1. DEFINITIONS

Unless otherwise defined, all technical and scientific terms used herein have the same meaning as commonly understood by one of ordinary skill in the art. In case of conflict, the present document, including definitions, will control. Exemplary methods and materials are described herein, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"Antibody" may mean an antibody of classes IgG, IgM, IgA, IgD or IgE, or fragments, fragments or derivatives thereof, including Fab, F(ab')2, Fd, and single chain antibodies, and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

"Antigen" refers to proteins that have the ability to generate an immune response in a host. An antigen may be recognized and bound by an antibody. An antigen may originate from within the body or from the external environment.

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th Ed., U.S. Department of Health and Human Services, National Institutes of Health (1987). There are three heavy chain and three light chain CDRs (or CDR regions) in the variable portion of an immunoglobulin. Thus, "CDRs" as used herein refers to all three heavy chain CDRs, or all three light chain CDRs (or both all heavy and all light chain CDRs, if appropriate). The structure and protein folding of the antibody may mean that other residues are considered part of the antigen binding region and would be understood to be so by a skilled person. See for example Chothia et al., (1989) Conformations of immunoglobulin hypervariable regions; Nature 342, p 877-883.

"Antibody fragment" or "fragment of an antibody" as used interchangeably herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

"Adjuvant" as used herein means any molecule added to the vaccine described herein to enhance the immunogenicity of the antigen.

"Coding sequence" or "encoding nucleic acid" as used herein may refer to the nucleic acid (RNA or DNA molecule) that comprise a nucleotide sequence which encodes an antibody as set forth herein. The coding sequence may also comprise a DNA sequence which encodes an RNA sequence. The coding sequence may further include initiation and termination signals operably linked to regulatory elements including a promoter and polyadenylation signal capable of directing expression in the cells of an individual or mammal to whom the nucleic acid is administered. The coding sequence may further include sequences that encode signal peptides.

"Complement" or "complementary" as used herein may mean a nucleic acid may have Watson-Crick (e.g., A-T/U and C-G) or Hoogsteen base pairing between nucleotides or nucleotide analogs of nucleic acid molecules.

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

"Endogenous antibody" as used herein may refer to an antibody that is generated in a subject that is administered an effective dose of an antigen for induction of a humoral immune response.

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

"Fragment" may mean a polypeptide fragment of an antibody that is function, i.e., can bind to desired target and have the same intended effect as a full length antibody. A fragment of an antibody may be 100% identical to the full length except missing at least one amino acid from the N and/or C terminal, in each case with or without signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length antibody, excluding any heterologous signal peptide added. The fragment may comprise a fragment of a polypeptide that is 95% or more, 96% or more, 97% or more, 98% or more or 99% or more identical to the antibody and additionally comprise an N terminal methionine or heterologous signal peptide which is not included when calculating percent identity. Fragments may further comprise an N terminal methionine and/or a signal peptide such as an immunoglobulin signal peptide, for example an IgE or IgG signal peptide. The N terminal methionine and/or signal peptide may be linked to a fragment of an antibody.

A fragment of a nucleic acid sequence that encodes an antibody may be 100% identical to the full length except missing at least one nucleotide from the 5' and/or 3' end, in each case with or without sequences encoding signal peptides and/or a methionine at position 1. Fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length coding sequence, excluding any heterologous signal peptide added. The fragment may comprise a fragment that encode a polypeptide that is 95% or more, 96% or more, 97% or more, 98% or more or 99% or more identical to the antibody and additionally optionally comprise sequence encoding an N terminal methionine or heterologous signal peptide which is not included when calculating percent identity. Fragments may further comprise coding sequences for an N terminal methionine and/or a signal peptide such as an immunoglobulin signal peptide, for example an IgE or IgG signal peptide. The coding sequence encoding the N terminal methionine and/or signal peptide may be linked to a fragment of coding sequence.

"Genetic construct" as used herein refers to the DNA or RNA molecules that comprise a nucleotide sequence which encodes a protein, such as an antibody. The genetic construct may also refer to a DNA molecule which transcribes an RNA. The coding sequence includes initiation and termination signals operably linked to regulatory elements including a promoter and polyadenylation signal capable of directing expression in the cells of the individual to whom the nucleic acid molecule is administered. As used herein, the term "expressible form" refers to gene constructs that contain the necessary regulatory elements operable linked to a coding sequence that encodes a protein such that when present in the cell of the individual, the coding sequence will be expressed.

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Impedance" as used herein may be used when discussing the feedback mechanism and can be converted to a current value according to Ohm's law, thus enabling comparisons with the preset current.

"Immune response" as used herein may mean the activation of a host's immune system, e.g., that of a mammal, in response to the introduction of one or more nucleic acids and/or peptides. The immune response can be in the form of a cellular or humoral response, or both.

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

A "peptide," "protein," or "polypeptide" as used herein can mean a linked sequence of amino acids and can be natural, synthetic, or a modification or combination of natural and synthetic.

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV 40 late promoter and the CMV IE promoter.

"Signal peptide" and "leader sequence" are used interchangeably herein and refer to an amino acid sequence that can be linked at the amino terminus of a protein set forth herein. Signal peptides/leader sequences typically direct localization of a protein. Signal peptides/leader sequences used herein may facilitate secretion of the protein from the cell in which it is produced. Signal peptides/leader sequences are often cleaved from the remainder of the protein, often referred to as the mature protein, upon secretion from the cell. Signal peptides/leader sequences are linked at the N terminus of the protein.

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Substantially complementary" as used herein may mean that a first sequence is at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

"Substantially identical" as used herein may mean that a first and second sequence are at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% identical over a region of 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, 200, 300, 400, 500, 600, 700, 800, 900, 1000, 1100 or more nucleotides or amino acids, or with respect to nucleic acids, if the first sequence is substantially complementary to the complement of the second sequence.

"Synthetic antibody" as used herein refers to an antibody that is encoded by the recombinant nucleic acid sequence described herein and is generated in a subject.

"Treatment" or "treating," as used herein can mean protecting of a subject from a disease through means of preventing, suppressing, repressing, or completely eliminating the disease. Preventing the disease involves administering a vaccine of the present invention to a subject prior to onset of the disease. Suppressing the disease involves administering a vaccine of the present invention to a subject after induction of the disease but before its clinical appearance. Repressing the disease involves administering a vaccine of the present invention to a subject after clinical appearance of the disease.

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide, may indicate that the peptide or polypeptide differs in amino acid sequence by the insertion, deletion, or conservative substitution of amino acids, but retains at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

A variant may be a nucleic acid sequence that is substantially identical over the full length of the full gene sequence or a fragment thereof. The nucleic acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant may be an amino acid sequence that is substantially identical over the full length of the amino acid sequence or fragment thereof. The amino acid sequence may be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

"Vector" as used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated. This applies regardless of the breadth of the range.

2. COMPOSITIONS

The invention also includes novel sequences for use for producing antibodies. In one embodiment, the antibodies of the invention can be produced in mammalian cells or for delivery in DNA or RNA vectors including bacterial, yeast, as well as viral vectors.

The present invention relates to a composition comprising a recombinant nucleic acid sequence encoding an antibody, a fragment thereof, a variant thereof, or a combination thereof. The composition, when administered to a subject in need thereof, can result in the generation of a synthetic antibody in the subject. The synthetic antibody can bind a target molecule (i.e., an antigen, such as PCSK9) present in the subject. Such binding can neutralize the antigen, block recognition of the antigen by another molecule, for example, a protein or nucleic acid, and elicit or induce an immune response to the antigen.

In one embodiment, the composition comprises a nucleotide sequence encoding a synthetic antibody. In one embodiment, the composition comprises a nucleic acid molecule comprising a first nucleotide sequence encoding a first synthetic antibody and a second nucleotide sequence encoding a second synthetic antibody. In one embodiment, the nucleic acid molecule comprises a nucleotide sequence encoding a cleavage domain.

In one embodiment, the nucleic acid molecule comprises a nucleotide sequence encoding one or more anti-PCSK9 antibodies.

In one embodiment, the nucleotide sequence encoding an anti-PCSK9 antibody comprises one or more codon optimized nucleic acid sequences encoding one or more amino acid sequences as set forth in SEQ ID NOs: 1, 3, 5, 7, or a fragment of one or more amino acid sequences as set forth in SEQ ID NOs: 1, 3, 5, and 7.

In one embodiment, the nucleotide sequence has at least about 80% identity over the entire length of at least one nucleotide sequence selected from the group of SEQ ID NOs: 2, 4,8 and 6.

In one embodiment, the nucleotide sequence encoding an anti-PCSK9 antibody comprises one or more RNA sequences transcribed from one or more DNA sequences encoding an amino acid sequence at least 90% homologous to one or more of SEQ ID NOs: 1, 3, 5, and 7, or a fragment of an amino acid sequence at least 90% homologous to one or more of SEQ ID NOs: 1, 3, 5, and 7. In one embodiment, the nucleotide sequence encoding an anti-PCSK9 antibody comprises one or more RNA sequences transcribed from one or more DNA sequences encoding an amino acid sequence as set forth in SEQ ID NOs: 1, 3, 5, and 7, or a fragment of an amino acid sequence as set forth in SEQ ID NOs: 1, 3, 5, and 7.

In one embodiment, the nucleotide sequence encoding an anti-PCSK9 antibody comprises one or more codon optimized nucleic acid sequences at least 90% homologous to one or more nucleic acid sequences encoding one or more of SEQ ID NOs: 1, 3, 5, and 7, or a fragment of a nucleic acid sequence at least 90% homologous to one or more nucleic acid sequences encoding one or more of SEQ ID NOs: 1, 3, 5, and 7.

The composition of the invention can treat, prevent, and/or protect against any disease, disorder, or condition associated with PCSK9 activity. In certain embodiments, the composition can treat, prevent, and/or protect against cardiovascular diseases and disorders.

In one embodiment, the composition of the invention is provided in combination with at least one other agent, such as an antigen. In one embodiment, a combination can be a single formulation or can be separate formulations and administered in sequence (either antigen first and then anti-PCSK9 antibody, or anti-PCSK9 antibody first and then antigen). The composition can increase antigen presentation and the overall immune response to the antigen in a subject. The combination of antigen and anti-PCSK9 antibody induces the immune system more efficiently than a composition comprising the antigen alone. This more efficient immune response provides increased efficacy in the treatment and/or prevention of a disease, such as cardiovascular disease.

The composition can result in the generation of the synthetic antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 36 hours, 48 hours, 60 hours, 72 hours, 84 hours, or 96 hours. The composition can be administered before or after administration of the antigen(s) to the subject. In some embodiments, the checkpoint inhibitor(s) can be administered at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 60 days, or 90 days before or after administration of the antigen(s) to the subject.

In still other embodiments, the checkpoint inhibitor(s) can be administered at least 1 week, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, or 15 weeks before or after administration of the antigen(s) to the subject. In other embodiments, the checkpoint inhibitor(s) can be administered about 12 hours to about 15 weeks, about 12 hours to about 10 weeks, about 12 hours to about 5 weeks, about 12 hours to about 1 week, about 12 hours to about 60 hours, about 12 hours to about 48 hours, about 24 hours to about 15 weeks, about 60 hours to about 15 weeks, about 96 hours to about 15 weeks, about 1 day to about 15 weeks, about 5 days to about 15 weeks, about 10 days to about 15 weeks, about 15 days to about 15 weeks, about 20 days to about 15 weeks, about 25 days to about 15 weeks, about 30 days to about 15 weeks, about 1 week to about 15 weeks, about 5 weeks to about 15 weeks, or about 10 weeks to about 15 weeks before or after administration of the antigen(s) to the subject.

The composition, when administered to the subject in need thereof, can result in the generation of the synthetic antibody in the subject more quickly than the generation of an endogenous antibody in a subject who is administered an antigen to induce a humoral immune response. The composition can result in the generation of the synthetic antibody at least about 1 day, 2 days, 3 days, 4 days, 5 days, 6 days, 7 days, 8 days, 9 days, or 10 days before the generation of the endogenous antibody in the subject who was administered an antigen to induce a humoral immune response.

The composition of the present invention can have features required of effective compositions such as being safe so that the composition does not cause illness or death; being protective against illness; and providing ease of administration, few side effects, biological stability, and low cost per dose.

a. Recombinant Nucleic Acid Sequence

As described above, the composition can comprise a recombinant nucleic acid sequence. The recombinant nucleic acid sequence can encode the antibody, a fragment thereof, a variant thereof, or a combination thereof. The antibody is described in more detail elsewhere herein.

The recombinant nucleic acid sequence can be a heterologous nucleic acid sequence. The recombinant nucleic acid sequence can include one or more heterologous nucleic acid sequences.

The recombinant nucleic acid sequence can be an optimized nucleic acid sequence. Such optimization can increase or alter the immunogenicity of the antibody. Optimization can also improve transcription and/or translation. Optimization can include one or more of the following: low GC content leader sequence to increase transcription; mRNA stability and codon optimization; addition of a kozak sequence (e.g., GCC ACC) for increased translation; addition of an immunoglobulin (Ig) leader sequence encoding a signal peptide; addition of an internal IRES sequence and eliminating to the extent possible cis-acting sequence motifs (i.e., internal TATA boxes).

b. Recombinant Nucleic Acid Sequence Construct

The recombinant nucleic acid sequence can include one or more recombinant nucleic acid sequence constructs. The recombinant nucleic acid sequence construct can include one or more components, which are described in more detail herein.

The recombinant nucleic acid sequence construct can include a heterologous nucleic acid sequence that encodes a heavy chain polypeptide, a fragment thereof, a variant thereof, or a combination thereof. The recombinant nucleic acid sequence construct can include a heterologous nucleic acid sequence that encodes a light chain polypeptide, a fragment thereof, a variant thereof, or a combination thereof. The recombinant nucleic acid sequence construct can also include a heterologous nucleic acid sequence that encodes a protease or peptidase cleavage site. The recombinant nucleic acid sequence construct can also include a heterologous nucleic acid sequence that encodes an internal ribosome entry site (IRES). An IRES may be either a viral IRES or a eukaryotic IRES. The recombinant nucleic acid sequence construct can include one or more leader sequences, in which each leader sequence encodes a signal peptide. The recombinant nucleic acid sequence construct can include one or more promoters, one or more introns, one or more transcription termination regions, one or more initiation codons, one or more termination or stop codons, and/or one or more polyadenylation signals. The recombinant nucleic acid sequence construct can also include one or more linker or tag sequences. The tag sequence can encode a hemagglutinin (HA) tag.

(1) Heavy Chain Polypeptide

The recombinant nucleic acid sequence construct can include the heterologous nucleic acid encoding the heavy chain polypeptide, a fragment thereof, a variant thereof, or a combination thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), and a constant heavy chain region 3 (CH3), and/or a hinge region.

In some embodiments, the heavy chain polypeptide can include a VH region and a CH1 region. In other embodiments, the heavy chain polypeptide can include a VH region, a CH1 region, a hinge region, a CH2 region, and a CH3 region.

The heavy chain polypeptide can include a complementarity determining region ("CDR") set. The CDR set can contain three hypervariable regions of the VH region. Proceeding from N-terminus of the heavy chain polypeptide, these CDRs are denoted "CDR1," "CDR2," and "CDR3," respectively. CDR1, CDR2, and CDR3 of the heavy chain polypeptide can contribute to binding or recognition of the antigen.

(2) Light Chain Polypeptide

The recombinant nucleic acid sequence construct can include the heterologous nucleic acid sequence encoding the light chain polypeptide, a fragment thereof, a variant thereof, or a combination thereof. The light chain polypeptide can include a variable light chain (VL) region and/or a constant light chain (CL) region.

The light chain polypeptide can include a complementarity determining region ("CDR") set. The CDR set can contain three hypervariable regions of the VL region. Proceeding from N-terminus of the light chain polypeptide, these CDRs are denoted "CDR1," "CDR2," and "CDR3," respectively. CDR1, CDR2, and CDR3 of the light chain polypeptide can contribute to binding or recognition of the antigen.

(3) Protease Cleavage Site

The recombinant nucleic acid sequence construct can include heterologous nucleic acid sequence encoding a protease cleavage site. The protease cleavage site can be recognized by a protease or peptidase. The protease can be an endopeptidase or endoprotease, for example, but not limited to, furin, elastase, HtrA, calpain, trypsin, chymotrypsin, trypsin, and pepsin. The protease can be furin. In other embodiments, the protease can be a serine protease, a threonine protease, cysteine protease, aspartate protease, metalloprotease, glutamic acid protease, or any protease that cleaves an internal peptide bond (i.e., does not cleave the N-terminal or C-terminal peptide bond).

The protease cleavage site can include one or more amino acid sequences that promote or increase the efficiency of cleavage. The one or more amino acid sequences can promote or increase the efficiency of forming or generating discrete polypeptides. The one or more amino acids sequences can include a 2A peptide sequence.

(4) Linker Sequence

The recombinant nucleic acid sequence construct can include one or more linker sequences. The linker sequence can spatially separate or link the one or more components described herein. In other embodiments, the linker sequence can encode an amino acid sequence that spatially separates or links two or more polypeptides.

(5) Promoter

The recombinant nucleic acid sequence construct can include one or more promoters. The one or more promoters may be any promoter that is capable of driving gene expression and regulating gene expression. Such a promoter is a cis-acting sequence element required for transcription via a DNA dependent RNA polymerase. Selection of the promoter used to direct gene expression depends on the particular application. The promoter may be positioned about the same distance from the transcription start in the recombinant nucleic acid sequence construct as it is from the transcription start site in its natural setting. However, variation in this distance may be accommodated without loss of promoter function.

The promoter may be operably linked to the heterologous nucleic acid sequence encoding the heavy chain polypeptide and/or light chain polypeptide. The promoter may be a promoter shown effective for expression in eukaryotic cells. The promoter operably linked to the coding sequence may be a CMV promoter, a promoter from simian virus 40 (SV40), such as SV40 early promoter and SV40 later promoter, a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, human polyhedrin, or human metalothenein.

The promoter can be a constitutive promoter or an inducible promoter, which initiates transcription only when the host cell is exposed to some particular external stimulus. In the case of a multicellular organism, the promoter can also be specific to a particular tissue or organ or stage of development. The promoter may also be a tissue specific promoter, such as a muscle or skin specific promoter, natural or synthetic. Examples of such promoters are described in US patent application publication no. US20040175727, the contents of which are incorporated herein in its entirety.

The promoter can be associated with an enhancer. The enhancer can be located upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

(6) Intron

The recombinant nucleic acid sequence construct can include one or more introns. Each intron can include functional splice donor and acceptor sites. The intron can include an enhancer of splicing. The intron can include one or more signals required for efficient splicing.

(7) Transcription Termination Region

The recombinant nucleic acid sequence construct can include one or more transcription termination regions. The transcription termination region can be downstream of the coding sequence to provide for efficient termination. The transcription termination region can be obtained from the same gene as the promoter described herein or can be obtained from one or more different genes.

(8) Initiation Codon

The recombinant nucleic acid sequence construct can include one or more initiation codons. The initiation codon can be located upstream of the coding sequence. The initiation codon can be in frame with the coding sequence. The initiation codon can be associated with one or more signals required for efficient translation initiation, for example, but not limited to, a ribosome binding site.

(9) Termination Codon

The recombinant nucleic acid sequence construct can include one or more termination or stop codons. The termination codon can be downstream of the coding sequence. The termination codon can be in frame with the coding sequence. The termination codon can be associated with one or more signals required for efficient translation termination.

(10) Polyadenylation Signal

The recombinant nucleic acid sequence construct can include one or more polyadenylation signals. The polyadenylation signal can include one or more signals required for efficient polyadenylation of the transcript. The polyadenylation signal can be positioned downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, CA).

(11) Leader Sequence

The recombinant nucleic acid sequence construct can include one or more leader sequences. The leader sequence can encode a signal peptide. The signal peptide can be an immunoglobulin (Ig) signal peptide, for example, but not limited to, an IgG signal peptide and a IgE signal peptide.

c. Arrangement of the Recombinant Nucleic Acid Sequence Construct

As described above, the recombinant nucleic acid sequence can include one or more recombinant nucleic acid sequence constructs, in which each recombinant nucleic acid sequence construct can include one or more components. The one or more components are described in detail above. The one or more components, when included in the recombinant nucleic acid sequence construct, can be arranged in any order relative to one another. In some embodiments, the one or more components can be arranged in the recombinant nucleic acid sequence construct as described herein.

(1) Arrangement 1

In one arrangement, a first recombinant nucleic acid sequence construct can include the heterologous nucleic acid sequence encoding the heavy chain polypeptide and a second recombinant nucleic acid sequence construct can include the heterologous nucleic acid sequence encoding the light chain polypeptide.

The first recombinant nucleic acid sequence construct can be placed in a vector. The second recombinant nucleic acid sequence construct can be placed in a second or separate vector. Placement of the recombinant nucleic acid sequence construct into the vector is described in more detail herein.

The first recombinant nucleic acid sequence construct can also include the promoter, intron, transcription termination region, initiation codon, termination codon, and/or polyadenylation signal. The first recombinant nucleic acid sequence construct can further include the leader sequence, in which the leader sequence is located upstream (or 5') of the heterologous nucleic acid sequence encoding the heavy chain polypeptide. Accordingly, the signal peptide encoded by the leader sequence can be linked by a peptide bond to the heavy chain polypeptide.

The second recombinant nucleic acid sequence construct can also include the promoter, initiation codon, termination codon, and polyadenylation signal. The second recombinant nucleic acid sequence construct can further include the leader sequence, in which the leader sequence is located upstream (or 5') of the heterologous nucleic acid sequence encoding the light chain polypeptide. Accordingly, the signal peptide encoded by the leader sequence can be linked by a peptide bond to the light chain polypeptide.

Accordingly, one example of arrangement 1 can include the first vector (and thus first recombinant nucleic acid sequence construct) encoding the heavy chain polypeptide that includes VH and CH1, and the second vector (and thus second recombinant nucleic acid sequence construct) encoding the light chain polypeptide that includes VL and CL. A second example of arrangement 1 can include the first vector (and thus first recombinant nucleic acid sequence construct) encoding the heavy chain polypeptide that includes VH, CH1, hinge region, CH2, and CH3, and the second vector (and thus second recombinant nucleic acid sequence construct) encoding the light chain polypeptide that includes VL and CL.

(2) Arrangement 2

In a second arrangement, the recombinant nucleic acid sequence construct can include the heterologous nucleic acid sequence encoding the heavy chain polypeptide and the heterologous nucleic acid sequence encoding the light chain polypeptide. The heterologous nucleic acid sequence encoding the heavy chain polypeptide can be positioned upstream (or 5') of the heterologous nucleic acid sequence encoding the light chain polypeptide. Alternatively, the heterologous nucleic acid sequence encoding the light chain polypeptide can be positioned upstream (or 5') of the heterologous nucleic acid sequence encoding the heavy chain polypeptide.

The recombinant nucleic acid sequence construct can be placed in the vector as described in more detail herein.

The recombinant nucleic acid sequence construct can include the heterologous nucleic acid sequence encoding the protease cleavage site and/or the linker sequence. If included in the recombinant nucleic acid sequence construct, the heterologous nucleic acid sequence encoding the protease cleavage site can be positioned between the heterologous nucleic acid sequence encoding the heavy chain polypeptide and the heterologous nucleic acid sequence encoding the light chain polypeptide. Accordingly, the protease cleavage site allows for separation of the heavy chain polypeptide and the light chain polypeptide into distinct polypeptides upon expression. In other embodiments, if the linker sequence is included in the recombinant nucleic acid sequence construct, then the linker sequence can be positioned between the heterologous nucleic acid sequence encoding the heavy chain polypeptide and the heterologous nucleic acid sequence encoding the light chain polypeptide.

The recombinant nucleic acid sequence construct can also include the promoter, intron, transcription termination region, initiation codon, termination codon, and/or polyadenylation signal. The recombinant nucleic acid sequence construct can include one or more promoters. The recombinant nucleic acid sequence construct can include two promoters such that one promoter can be associated with the heterologous nucleic acid sequence encoding the heavy chain polypeptide and the second promoter can be associated with the heterologous nucleic acid sequence encoding the light chain polypeptide. In still other embodiments, the recombinant nucleic acid sequence construct can include one promoter that is associated with the heterologous nucleic acid sequence encoding the heavy chain polypeptide and the heterologous nucleic acid sequence encoding the light chain polypeptide.

The recombinant nucleic acid sequence construct can further include two leader sequences, in which a first leader sequence is located upstream (or 5') of the heterologous nucleic acid sequence encoding the heavy chain polypeptide and a second leader sequence is located upstream (or 5') of the heterologous nucleic acid sequence encoding the light chain polypeptide. Accordingly, a first signal peptide encoded by the first leader sequence can be linked by a peptide bond to the heavy chain polypeptide and a second signal peptide encoded by the second leader sequence can be linked by a peptide bond to the light chain polypeptide.

Accordingly, one example of arrangement 2 can include the vector (and thus recombinant nucleic acid sequence construct) encoding the heavy chain polypeptide that includes VH and CH1, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A second example of arrangement of 2 can include the vector (and thus recombinant nucleic acid sequence construct) encoding the heavy chain polypeptide that includes VH and CH1, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

A third example of arrangement 2 can include the vector (and thus recombinant nucleic acid sequence construct) encoding the heavy chain polypeptide that includes VH, CH1, hinge region, CH2, and CH3, and the light chain polypeptide that includes VL and CL, in which the linker sequence is positioned between the heterologous nucleic acid sequence encoding the heavy chain polypeptide and the heterologous nucleic acid sequence encoding the light chain polypeptide.

A fourth example of arrangement of 2 can include the vector (and thus recombinant nucleic acid sequence construct) encoding the heavy chain polypeptide that includes VH, CH1, hinge region, CH2, and CH3, and the light chain polypeptide that includes VL and CL, in which the heterologous nucleic acid sequence encoding the protease cleavage site is positioned between the heterologous nucleic acid sequence encoding the heavy chain polypeptide and the heterologous nucleic acid sequence encoding the light chain polypeptide.

d. Expression from the Recombinant Nucleic Acid Sequence Construct

As described above, the recombinant nucleic acid sequence construct can include, amongst the one or more components, the heterologous nucleic acid sequence encoding the heavy chain polypeptide and/or the heterologous nucleic acid sequence encoding the light chain polypeptide. Accordingly, the recombinant nucleic acid sequence construct can facilitate expression of the heavy chain polypeptide and/or the light chain polypeptide.

When arrangement 1 as described above is utilized, the first recombinant nucleic acid sequence construct can facilitate the expression of the heavy chain polypeptide and the second recombinant nucleic acid sequence construct can facilitate expression of the light chain polypeptide. When arrangement 2 as described above is utilized, the recombinant nucleic acid sequence construct can facilitate the expression of the heavy chain polypeptide and the light chain polypeptide.

Upon expression, for example, but not limited to, in a cell, organism, or mammal, the heavy chain polypeptide and the light chain polypeptide can assemble into the synthetic antibody. In particular, the heavy chain polypeptide and the light chain polypeptide can interact with one another such that assembly results in the synthetic antibody being capable of binding the antigen. In other embodiments, the heavy chain polypeptide and the light chain polypeptide can interact with one another such that assembly results in the synthetic antibody being more immunogenic as compared to an antibody not assembled as described herein. In still other embodiments, the heavy chain polypeptide and the light chain polypeptide can interact with one another such that assembly results in the synthetic antibody being capable of eliciting or inducing an immune response against the antigen.

e. Vectors

The recombinant nucleic acid sequence construct described above can be placed in one or more vectors. The one or more vectors can contain an origin of replication. The one or more vectors can be a plasmid, bacteriophage, bacterial artificial chromosome or yeast artificial chromosome. The one or more vectors can be either a self-replication extra chromosomal vector, or a vector which integrates into a host genome.

Vectors include, but are not limited to, plasmids, expression vectors, recombinant viruses, any form of recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include, but are not limited to replicons (e.g., RNA replicons, bacteriophages) to which fragments of DNA may be attached and become replicated. Vectors thus include, but are not limited to RNA, autonomous self-replicating circular or linear DNA or RNA (e.g., plasmids, viruses, and the like, see, e.g., U.S. Pat. No. 5,217,879), and include both the expression and non-expression plasmids. In some embodiments, the vector includes linear DNA, enzymatic DNA or synthetic DNA. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The one or more vectors can be a heterologous expression construct, which is generally a plasmid that is used to introduce a specific gene into a target cell. Once the expression vector is inside the cell, the heavy chain polypeptide and/or light chain polypeptide that are encoded by the recombinant nucleic acid sequence construct is produced by the cellular-transcription and translation machinery ribosomal complexes. The one or more vectors can express large amounts of stable messenger RNA, and therefore proteins.

(1) Expression Vector

The one or more vectors can be a circular plasmid or a linear nucleic acid. The circular plasmid and linear nucleic acid are capable of directing expression of a particular nucleotide sequence in an appropriate subject cell. The one or more vectors comprising the recombinant nucleic acid sequence construct may be chimeric, meaning that at least one of its components is heterologous with respect to at least one of its other components.

(2) Plasmid

The one or more vectors can be a plasmid. The plasmid may be useful for transfecting cells with the recombinant nucleic acid sequence construct. The plasmid may be useful for introducing the recombinant nucleic acid sequence construct into the subject. The plasmid may also comprise a regulatory sequence, which may be well suited for gene expression in a cell into which the plasmid is administered.

The plasmid may also comprise a mammalian origin of replication in order to maintain the plasmid extrachromosomally and produce multiple copies of the plasmid in a cell. The plasmid may be pVAX, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may be pSE420 (Invitrogen, San Diego, Calif.), which may be used for protein production in *Escherichia coli* (*E. coli*). The plasmid may also be p YES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNAI or pcDNA3 (Invitrogen, San Diego, Calif.), which may be used for protein production in mammalian cells such as Chinese hamster ovary (CHO) cells.

(3) RNA

In one embodiment, the nucleic acid is an RNA molecule. In one embodiment, the RNA molecule is transcribed from a DNA sequence described herein. For example, in some embodiments, the RNA molecule is encoded by a DNA sequence at least 90% homologous to a DNA sequence encoding one of SEQ ID NOs: 1, 3, 5, 7, or a variant thereof or a fragment thereof. Accordingly, in one embodiment, the invention provides an RNA molecule encoding one or more of the MAbs or DMAbs. The RNA may be plus-stranded. Accordingly, in some embodiments, the RNA molecule can be translated by cells without needing any intervening replication steps such as reverse transcription. A RNA molecule useful with the invention may have a 5' cap (e.g. a 7-methylguanosine). This cap can enhance in vivo translation of the RNA. The 5' nucleotide of a RNA molecule useful with the invention may have a 5' triphosphate group. In a capped RNA this may be linked to a 7-methylguanosine via a 5'-to-5' bridge. A RNA molecule may have a 3' poly-A tail. It may also include a poly-A polymerase recognition sequence (e.g. AAUAAA) near its 3' end. A RNA molecule useful with the invention may be single-stranded. A RNA molecule useful with the invention may comprise synthetic RNA. In some embodiments, the RNA molecule is a naked RNA molecule. In one embodiment, the RNA molecule is comprised within a vector.

In one embodiment, the RNA has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of RNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many RNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the RNA.

In one embodiment, the RNA has both a cap on the 5' end and a 3' poly(A) tail which determine ribosome binding, initiation of translation and stability of RNA in the cell.

In one embodiment, the RNA is a nucleoside-modified RNA. Nucleoside-modified RNA have particular advantages over non-modified RNA, including for example, increased stability, low or absent innate immunogenicity, and enhanced translation.

(4) Circular and Linear Vector

The one or more vectors may be one or more circular plasmids, which may transform a target cell by integration into the cellular genome or exist extrachromosomally (e.g., autonomous replicating plasmid with an origin of replication). The vector can be pVAX, pcDNA3.0, or provax, or any other expression vector capable of expressing the heavy chain polypeptide and/or light chain polypeptide encoded by the recombinant nucleic acid sequence construct.

Also provided herein is a linear nucleic acid, or linear expression cassette ("LEC"), that is capable of being efficiently delivered to a subject via electroporation and expressing the heavy chain polypeptide and/or light chain polypeptide encoded by the recombinant nucleic acid sequence construct. The LEC may be any linear DNA devoid of any phosphate backbone. The LEC may not contain any antibiotic resistance genes and/or a phosphate backbone. The LEC may not contain other nucleic acid sequences unrelated to the desired gene expression.

The LEC may be derived from any plasmid capable of being linearized. The plasmid may be capable of expressing the heavy chain polypeptide and/or light chain polypeptide encoded by the recombinant nucleic acid sequence construct. The plasmid can be pNP (Puerto Rico/34) or pM2 (New Caledonia/99). The plasmid may be WLV009, pVAX, pcDNA3.0, or provax, or any other expression vector capable of expressing the heavy chain polypeptide and/or light chain polypeptide encoded by the recombinant nucleic acid sequence construct.

The LEC can be perM2. The LEC can be perNP. perNP and perMR can be derived from pNP (Puerto Rico/34) and pM2 (New Caledonia/99), respectively.

(5) Viral Vectors

In one embodiment, viral vectors are provided herein which are capable of delivering a nucleic acid of the invention to a cell. The expression vector may be provided to a cell in the form of a viral vector. Viral vector technology is well known in the art and is described, for example, in Sambrook et al. (2001), and in Ausubel et al. (1997), and in other virology and molecular biology manuals. Viruses, which are useful as vectors include, but are not limited to, retroviruses, adenoviruses, adeno-associated viruses, herpes viruses, and lentiviruses. In general, a suitable vector comprises an origin of replication functional in at least one organism, a promoter sequence, convenient restriction endonuclease sites, and one or more selectable markers. (See, e.g., WO 01/96584; WO 01/29058; and U.S. Pat. No. 6,326,193). Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

(6) Method of Preparing the Vector

Provided herein is a method for preparing the one or more vectors in which the recombinant nucleic acid sequence construct has been placed. After the final subcloning step, the vector can be used to inoculate a cell culture in a large scale fermentation tank, using known methods in the art.

In other embodiments, after the final subcloning step, the vector can be used with one or more electroporation (EP) devices. The EP devices are described herein in more herein.

The one or more vectors can be formulated or manufactured using a combination of known devices and techniques, and may be manufactured using a plasmid manufacturing technique that is described in U.S. provisional application U.S. Ser. No. 60/939,792, which was filed on May 23, 2007. In some examples, the DNA plasmids described herein can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

3. ANTIBODY

As described herein, the recombinant nucleic acid sequence can encode the antibody, a fragment thereof, a variant thereof, or a combination thereof. The antibody can bind or react with the antigen, which is described in more detail herein.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can treat, prevent, and/or protect against disease, such as cardiovascular disease or hypercholesterolemia, in the subject administered a composition of the invention. The antibody, by binding the antigen, can treat, prevent, and/or protect against disease in the subject administered the composition. The antibody can promote survival of the disease in the subject administered the composition. In one embodiment, the antibody can provide increased survival of the disease in the subject over the expected survival of a subject having the disease who has not been administered the antibody. In various embodiments, the antibody can provide at least about a 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or a 100% increase in survival of the disease in subjects administered the composition over the expected survival in the absence of the composition. In one embodiment, the antibody can provide increased protection against the disease in the subject over the expected protection of a subject who has not been administered the antibody. In various embodiments, the antibody can protect against disease in at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% of subjects administered the composition over the expected protection in the absence of the composition.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites. Accordingly, the antibody can be the Fab or F(ab')2. The Fab can include the heavy chain polypeptide and the light chain polypeptide. The heavy chain polypeptide of the Fab can include the VH region and the CH1 region. The light chain of the Fab can include the VL region and CL region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

The antibody can be a polyclonal or monoclonal antibody. The antibody can be a chimeric antibody, a single chain antibody, an affinity matured antibody, a human antibody, a humanized antibody, or a fully human antibody. The humanized antibody can be an antibody from a non-human species that binds the desired antigen having one or more complementarity determining regions (CDRs) from the non-human species and framework regions from a human immunoglobulin molecule.

The antibody can be a bispecific antibody as described herein in more detail. The antibody can be a bifunctional antibody as also described herein in more detail.

As described above, the antibody can be generated in the subject upon administration of the composition to the subject. The antibody may have a half-life within the subject. In some embodiments, the antibody may be modified to extend or shorten its half-life within the subject. Such modifications are described herein in more detail.

The antibody can be defucosylated as described in more detail herein.

The antibody may be modified to reduce or prevent antibody-dependent enhancement (ADE) of disease associated with the antigen as described in more detail herein.

a. Bispecific Antibody

The recombinant nucleic acid sequence can encode a bispecific antibody, a fragment thereof, a variant thereof, or a combination thereof. The bispecific antibody can bind or react with two antigens, for example, two of the antigens described herein in more detail. The bispecific antibody can be comprised of fragments of two of the antibodies described herein, thereby allowing the bispecific antibody to bind or react with two desired target molecules, which may include the antigen, which is described herein in more detail, a ligand, including a ligand for a receptor, a receptor, including a ligand-binding site on the receptor, a ligand-receptor complex, and a marker.

b. Bifunctional Antibody

The recombinant nucleic acid sequence can encode a bifunctional antibody, a fragment thereof, a variant thereof, or a combination thereof. The bifunctional antibody can bind or react with the antigen described herein. The bifunctional antibody can also be modified to impart an additional functionality to the antibody beyond recognition of and binding to the antigen. Such a modification can include, but is not limited to, coupling to factor H or a fragment thereof. Factor H is a soluble regulator of complement activation and thus, may contribute to an immune response via complement-mediated lysis (CML).

c. Extension of Antibody Half-Life

As described above, the antibody may be modified to extend or shorten the half-life of the antibody in the subject. The modification may extend or shorten the half-life of the antibody in the serum of the subject.

The modification may be present in a constant region of the antibody. The modification may be one or more amino acid substitutions in a constant region of the antibody that extend the half-life of the antibody as compared to a half-life of an antibody not containing the one or more amino acid substitutions. The modification may be one or more amino acid substitutions in the CH2 domain of the antibody that extend the half-life of the antibody as compared to a half-life of an antibody not containing the one or more amino acid substitutions.

In some embodiments, the one or more amino acid substitutions in the constant region may include replacing a methionine residue in the constant region with a tyrosine residue, a serine residue in the constant region with a threonine residue, a threonine residue in the constant region with a glutamate residue, or any combination thereof, thereby extending the half-life of the antibody.

In other embodiments, the one or more amino acid substitutions in the constant region may include replacing a methionine residue in the CH2 domain with a tyrosine residue, a serine residue in the CH2 domain with a threonine residue, a threonine residue in the CH2 domain with a glutamate residue, or any combination thereof, thereby extending the half-life of the antibody.

d. Defucosylation

The recombinant nucleic acid sequence can encode an antibody that is not fucosylated (i.e., a defucosylated antibody or a non-fucosylated antibody), a fragment thereof, a variant thereof, or a combination thereof. Fucosylation includes the addition of the sugar fucose to a molecule, for example, the attachment of fucose to N-glycans, 0-glycans and glycolipids. Accordingly, in a defucosylated antibody, fucose is not attached to the carbohydrate chains of the constant region. In turn, this lack of fucosylation may improve FcγRIIIa binding and antibody directed cellular cytotoxic (ADCC) activity by the antibody as compared to the fucosylated antibody. Therefore, in some embodiments, the non-fucosylated antibody may exhibit increased ADCC activity as compared to the fucosylated antibody.

The antibody may be modified so as to prevent or inhibit fucosylation of the antibody. In some embodiments, such a modified antibody may exhibit increased ADCC activity as compared to the unmodified antibody. The modification may be in the heavy chain, light chain, or a combination thereof. The modification may be one or more amino acid substitutions in the heavy chain, one or more amino acid substitutions in the light chain, or a combination thereof.

e. Reduced ADE Response

The antibody may be modified to reduce or prevent antibody-dependent enhancement (ADE) of disease associated with the antigen, but still neutralize the antigen.

In some embodiments, the antibody may be modified to include one or more amino acid substitutions that reduce or prevent binding of the antibody to FcγR1a. The one or more amino acid substitutions may be in the constant region of the antibody. The one or more amino acid substitutions may include replacing a leucine residue with an alanine residue in the constant region of the antibody, i.e., also known herein as LA, LA mutation or LA substitution. The one or more amino acid substitutions may include replacing two leucine residues, each with an alanine residue, in the constant region of the antibody and also known herein as LALA, LALA mutation, or LALA substitution. The presence of the LALA substitutions may prevent or block the antibody from binding to FcγR1a, and thus, the modified antibody does not enhance or cause ADE of disease associated with the antigen, but still neutralizes the antigen.

4. MONOCLONAL ANTIBODIES

In one embodiment, the invention provides anti-PCSK9 antibodies. The antibodies may be intact monoclonal antibodies, and immunologically active fragments (e.g., a Fab or (Fab)$_2$ fragment), a monoclonal antibody heavy chain, or a monoclonal antibody light chain.

The antibody may comprise a heavy chain and a light chain complementarity determining region ("CDR") set, respectively interposed between a heavy chain and a light chain framework ("FR") set which provide support to the CDRs and define the spatial relationship of the CDRs relative to each other. The CDR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region.

The antibody can be an immunoglobulin (Ig). The Ig can be, for example, IgA, IgM, IgD, IgE, and IgG. The immunoglobulin can include the heavy chain polypeptide and the light chain polypeptide. The heavy chain polypeptide of the immunoglobulin can include a VH region, a CH1 region, a hinge region, a CH2 region, and a CH3 region. The light chain polypeptide of the immunoglobulin can include a VL region and CL region.

5. METHOD OF GENERATING THE SYNTHETIC ANTIBODY

The present invention also relates a method of generating the synthetic antibody. The method can include administering the composition to the subject in need thereof by using the method of delivery described in more detail herein. Accordingly, the synthetic antibody is generated in the subject or in vivo upon administration of the composition to the subject.

The method can also include introducing the composition into one or more cells, and therefore, the synthetic antibody can be generated or produced in the one or more cells. The method can further include introducing the composition into one or more tissues, for example, but not limited to, skin and muscle, and therefore, the synthetic antibody can be generated or produced in the one or more tissues.

6. EXCIPIENTS AND OTHER COMPONENTS OF THE COMPOSITION

The composition may further comprise a pharmaceutically acceptable excipient. The pharmaceutically acceptable excipient can be functional molecules such as vehicles, adjuvants, carriers, or diluents. The pharmaceutically acceptable excipient can be a transfection facilitating agent, which can include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and the poly-L-glutamate may be present in the composition at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the composition. The composition may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. The transfection facilitating agent is a polyanion, polycation, including poly-L-glutamate (LGS), or lipid. Concentration of the transfection agent in the composition is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient can be an adjuvant in addition to the checkpoint inhibitor antibodies of the invention. The additional adjuvant can be other genes that are expressed in an alternative plasmid or are delivered as proteins in combination with the plasmid above in the composition. The adjuvant may be selected from the group consisting of: α-interferon(IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MEW, CD80, CD86 including IL-15 having the signal sequence deleted and optionally including the signal peptide from IgE. The adjuvant can be IL-12, IL-15, IL-28, CTACK, TECK, platelet derived growth factor (PDGF), TNFα, TNFβ, GM-CSF, epidermal growth factor (EGF), IL-1, IL-2, IL-4, IL-5, PD-1, IL-10, IL-12, IL-18, or a combination thereof.

Other genes that can be useful as adjuvants in addition to the antibodies of the invention include those encoding: MCP-1, MIP-1a, MIP-1p, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, IL-22, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof.

The composition may further comprise a genetic facilitator agent as described in U.S. Serial No. 021,579 filed Apr. 1, 1994, which is fully incorporated by reference.

The composition may comprise DNA at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, composition according to the present invention comprises about 5 nanogram to about 1000 micrograms of DNA. In some preferred embodiments, composition can contain about 10 nanograms to about 800 micrograms of DNA. In some preferred embodiments, the composition can contain about 0.1 to about 500 micrograms of DNA. In some preferred embodiments, the composition can contain about 1 to about 350 micrograms of DNA. In some preferred embodiments, the composition can contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of DNA.

The composition can be formulated according to the mode of administration to be used. An injectable pharmaceutical composition can be sterile, pyrogen free and particulate free. An isotonic formulation or solution can be used. Additives for isotonicity can include sodium chloride, dextrose, mannitol, sorbitol, and lactose. The composition can comprise a vasoconstriction agent. The isotonic solutions can include phosphate buffered saline. The composition can further comprise stabilizers including gelatin and albumin. The stabilizers can allow the formulation to be stable at room or ambient temperature for extended periods of time, including LGS or polycations or polyanions.

7. METHOD OF VACCINATION

The present invention is also directed to a method of increasing an immune response in a subject. Increasing the immune response can be used to treat and/or prevent disease in the subject. The method can include administering the herein disclosed vaccine to the subject. The subject administered the vaccine can have an increased or boosted immune response as compared to a subject administered the antigen alone. In some embodiments, the immune response can be increased by about 0.5-fold to about 15-fold, about 0.5-fold to about 10-fold, or about 0.5-fold to about 8-fold. Alternatively, the immune response in the subject administered the vaccine can be increased by at least about 0.5-fold, at least about 1.0-fold, at least about 1.5-fold, at least about 2.0-fold, at least about 2.5-fold, at least about 3.0-fold, at least about 3.5-fold, at least about 4.0-fold, at least about 4.5-fold, at least about 5.0-fold, at least about 5.5-fold, at least about 6.0-fold, at least about 6.5-fold, at least about 7.0-fold, at least about 7.5-fold, at least about 8.0-fold, at least about 8.5-fold, at least about 9.0-fold, at least about 9.5-fold, at least about 10.0-fold, at least about 10.5-fold, at least about 11.0-fold, at least about 11.5-fold, at least about 12.0-fold, at least about 12.5-fold, at least about 13.0-fold, at least about 13.5-fold, at least about 14.0-fold, at least about 14.5-fold, or at least about 15.0-fold.

In still other alternative embodiments, the immune response in the subject administered the vaccine can be increased about 50% to about 1500%, about 50% to about 1000%, or about 50% to about 800%. In other embodiments, the immune response in the subject administered the vaccine can be increased by at least about 50%, at least about 100%, at least about 150%, at least about 200%, at least about 250%, at least about 300%, at least about 350%, at least about 400%, at least about 450%, at least about 500%, at least about 550%, at least about 600%, at least about 650%, at least about 700%, at least about 750%, at least about 800%, at least about 850%, at least about 900%, at least about 950%, at least about 1000%, at least about 1050%, at least about 1100%, at least about 1150%, at least about 1200%, at least about 1250%, at least about 1300%, at least about 1350%, at least about 1450%, or at least about 1500%.

The vaccine dose can be between 1 μg to 10 mg active component/kg body weight/time, and can be 20 μg to 10 mg component/kg body weight/time. The vaccine can be administered every 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. The number of vaccine doses for effective treatment can be 1, 2, 3, 4, 5, 6, 7, 8, 9, or 10.

8. METHOD OF DELIVERY OF THE COMPOSITION

The present invention also relates to a method of delivering the composition to the subject in need thereof. The method of delivery can include, administering the composition to the subject. Administration can include, but is not limited to, DNA injection with and without in vivo electroporation, liposome mediated delivery, and nanoparticle facilitated delivery.

The mammal receiving delivery of the composition may be human, primate, non-human primate, cow, cattle, sheep, goat, antelope, bison, water buffalo, bison, bovids, deer, hedgehogs, elephants, llama, alpaca, mice, rats, and chicken.

The composition may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal, intranasal, intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The composition may be administered by traditional syringes, needleless injection devices, "microprojectile bombardment gone guns", or other physical methods such as electroporation ("EP"), "hydrodynamic method", or ultrasound.

a. Electroporation

Administration of the composition via electroporation may be accomplished using electroporation devices that can be configured to deliver to a desired tissue of a mammal, a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Plymouth Meeting, Pa.) or Elgen electroporator (Inovio Pharmaceuticals, Plymouth Meeting, Pa.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the composition of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the composition include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments, that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

9. CARDIOVASCULAR THERAPY

The invention provides methods of treating or preventing cardiovascular diseases or disorders, or of lowering low-density lipoprotein (LDL) levels. Related aspects of the invention provide methods of preventing, aiding in the prevention, and/or reducing diseases and disorders associated with PCSK9.

One aspect of the invention provides a method of lowering LDL-C in an individual in need thereof, the method comprising administering to the individual an effective amount of a composition of the invention. The invention further provides a method of treating or preventing a cardiovascular disease or disorder, hypercholesterolemia, dyslipidemia, atherosclerosis, CVD or coronary heart disease in an individual in need thereof, the method comprising administering to the individual an effective amount of any one of the compositions described herein.

In some embodiments of treating or preventing a cardiovascular disease or disorder, or of lowering LDL levels in an individual in need thereof, a second agent is administered to the individual. In one embodiment, the second agent comprises an second cardiovascular disease or hypercholesterolemia therapeutic. In some embodiments, the second agent comprises an agent inhibiting 3-hydroxy-3-methylglutaryl (HMG)-coenzyme A (CoA) thereby inducing a cellular depletion of cholesterol synthesis. For example, in one embodiment the second thereputic is cerivastatin, atorvastatin, simvastatin, pitavastatin, rosuvastatin, fluvastatin, lovastatin, or pravastatin. In some embodiments, the second agent comprises an agent inhibiting inhibits uptake and or bile acid re-absorption. For example, in one embodiment the second agent comprises cholestyramine, colestipol, or colesevelam. In some embodiments, the second agent comprises an agent that increases lipoprotein catabolism. For example, in one embodiment the second agent comprises niacin.

The compositions of the invention can be used to prevent, abate, minimize, control, and/or lessen cardiovascular disease or hypercholesterolemia in humans and animals. The compositions of the invention when administered to a subject in need of treatment can be used to reduce LDL levels. As such, the compositions of the invention can be administered as part of a combination therapy with one or more drugs or other pharmaceutical agents. When used as part of the combination therapy, the decrease in LDL levels afforded by the compositions of the invention allows for a more effective and efficient use of any pharmaceutical or drug therapy being used to treat the patient.

The following are non-limiting examples of diseases and disorders that can be treated by the methods and compositions of the invention: hypercholesterolemia, hyperlipidemia, dyslipidemia, atherosclerosis and cardiovascular diseases (CVD). In some embodiments, CVD or cardiovascular events include, but are not limited to, myocardial infarction, hospitalization for heart failure (HF), hospitalization for unstable angina, stroke, cardiovascular (CV) death, and hospitalization for revascularization.

In one embodiment, the invention provides a method to treat cardiovascular disease or hypercholesterolemia comprising treating the subject prior to, concurrently with, or subsequently to the treatment with a composition of the invention, with a complementary therapy for the cardiovascular disease or hypercholesterolemia.

In one embodiment, the invention provides a method to treat cardiovascular disease or hypercholesterolemia in an individual that is intolerant to statin treatment, the method comprising administering to the individual an effective amount of a composition of the invention The present invention is further illustrated in the following Examples. It should be understood that these Examples, while indicating exemplary embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims.

10. EXAMPLES

Example 1

Development of Novel DNA-Encoded PCSK9 Monoclonal Antibodies as Lipid-Lowering Therapeutics The data presented herein demonstrates a novel engineered a DNA-encoded mAb (DMAb) targeting PCSK9 (daPCSK9) which is useful as an alternative approach to protein-based lipid-lowering therapeutics. A single intramuscular administration of mouse daPCSK9 generated expression in vivo for over 42 days that corresponded with a substantial decrease of 28.6% in non-high-density lipoproteincholesterol (non-HDL-C) and 10.3% in total cholesterol by day 7 in wild-type mice. Repeated administrations of the DMAb plasmid led to increasing expression, with DMAb levels of 7.5 µg/mL at day 62. The data demonstrates that daPCSK9 therapeutics may provide a novel, simple, less frequent, cost-effective approach to reducing LDL-C, either as a stand-alone therapy or in combination with other LDL-lowering therapeutics for synergistic effect.

The materials and methods are now described.

Cell Culture

HEK293T, mouse hepatoma Hepa1-6, and human Huh-7 cells were maintained in DMEM (Gibco-Life Technologies) supplemented with 10% fetal bovine serum (FBS), 100 U/mL penicillin, and 100 µg/mL streptomycin (Life Technologies).

Anti-PCSK9 DMAb Plasmid Design and Construction

DMAb plasmids were designed to encode human or mouse anti-PCSK9 mAbs.

DMAb transgenes were designed in a single open reading frame, with the variable and constant heavy chains separated from variable and constant light chains by a furin/P2A cleavage site. Two constructs were developed: a human anti-PCSK9 DMAb (HdaPCSK9) on an IgG1 backbone, and a mouse anti-PCSK9 DMAb (MdaPCSK9) on an IgG2a backbone. DMAb transgenes were flanked with BamHI and XhoI restriction enzyme sites and synthesized by GenScript for subcloning into the corresponding restriction enzyme sites in a pVax-1 mammalian expression vector. Human CMV immediate-early promoter in the pVax-1 vector was used to drive the expression of the antibodies.

In Vitro Transfection of DMAb Plasmids

HEK293T, Hepa1-6, or Huh7 cells were transfected with anti-PCSK9 DMAb plasmids using lipofectamine LTX reagent and following the manufacturer's protocol. Briefly, $5 \times 10^5$ cells were seeded in a 12-well plate and incubated in a 37° C. incubator with 5% $CO_2$. Cells were transfected with 1 µg DMAb plasmid at 70% confluence and incubated for a maximum of 72 hr. DMAb expression following transfection was analyzed by western blot, ELISA, and immunofluorescencemicroscopy.

Western Blot and ELISA Analyses

A binding western blot analysis was performed to evaluate anti-PCSK9 DMAb-binding capability. Recombinant human or mouse PCSK9 protein (0.5-5 µg) was run in precast Bis-Tris gels (Invitrogen) under nonreducing conditions. Gels were transferred to Immobilon-FL polyvinylidene fluoride (PVDF) transfer membranes (Millipore). The membranes were blocked in Odyssey Blocking Buffer (LI-COR Biosciences) for 1 hr, then stained overnight at 4° C. with either supernatant from DMAb-transfected cells or serum from DMAb-treated mice, and compared to those of pVax-1-negative control samples. Membranes were washed with PBST (PBS with 0.05% Tween 20). Subsequently, membranes were stained with either anti-human or anti-mouse IgG 680RD antibody (LI-COR Biosciences) for 1 hour at room temperature (RT) and washed in PBST. Membranes were scanned on a LI-COR Odyssey CLx imager. 50 µg total sample protein was loaded in gels and run as described above for the analysis of liver lysates for LDLR expression. Membranes were stained with an anti-mLDLR primary antibody (AF2255; R&D Systems). Actin was stained using an anti-actin primary antibody (ab198991; Abcam) and an anti-rabbit IgG-HRP secondary antibody.

DMAbs with human backbones were quantified by an ELISA for total human IgG. ELISA MaxiSorp plates were coated with 1 µg/well anti-human IgG-Fc fragment antibody (A80-104A; Bethyl Laboratories) overnight at 4° C. Plates were blocked in 10% FBS in PBS for 1 hour at room temperature. Samples and recombinant human IgG standards were added to the plate for 1 hour at room temperature. After washing the plates, anti-human IgG-Fc fragment antibody-HRP (A80-104P; Bethyl Laboratories) was added for 1 hour at room temperature. SigmaFast OPD (Sigma-Aldrich) substrate solution was used for sample detection. Optical density was measured at 450 nm using a GloMax 96 Microplate Luminometer (Promega). For quantification of DMAbs with mouse backbones from cell supernatants, plates were coated with anti-mouse IgG-Fc fragment antibody (A90-131A; Bethyl Laboratories). Anti-mouse IgG-HRP (62-6520; Invitrogen) was used for detection. Serum samples of DMAbs with a mouse backbone were differentiated from background mouse IgGs by coating ELISA plates with recombinant PCSK9 protein. Purified recombinant anti-PCSK9 mAb was used as the standard. Quantitative ELISA data are expressed as ±SEM (n=3).

Immunofluorescence Analysis

Hepa1-6 cells were transfected with anti-PCSK9 DMAbs using lipofectamine LTX reagent as described above. 48 hours after transfection, cells were washed in PBS and fixed in 4% paraformaldehyde for 10 minutes at room temperature. Cells were then washed and incubated with anti-human IgG-FITC (A80-319F; Bethyl Laboratories) for 1 hr. After washing, cells were stained with DAPI nuclear stain and imaged on an EVOS FL Imaging System.

Flow Cytometry Analysis

Flow cytometry was used for the detection of LDLR on Huh7 cells transfected with control pVax-1 or anti-PCSK9 DMAb plasmids. 72 hours post-transfection, cells were washed with fluorescence-activated cell sorting (FACS) buffer (3% FBS in PBS) and stained with anti-LDLR primary antibody (ab52818; Abcam) for 1 hour at 4° C., followed by anti-rabbit IgG-FITC secondary antibody (ab6717; Abcam) for 1 hour at 4° C. Cells were washed 3 times in FACS buffer and fixed in 2% paraformaldehyde. Cells were analyzed on an LSR18 flow cytometer (BD Biosciences).

Immunohistochemistry of Mouse Muscle

Mouse anterior tibialis muscle sections were resected and embedded in paraffin. Paraffin-embedded samples were treated with antigen retrieval reagent and deparaffinized. Slides were then fixed with acetone and washed with PBS, followed by blocking and staining the sections with anti-human IgG antibody-HRP.

In Vivo DMAb Plasmid Administration

Evaluation of DMAbs was carried out in 6- to 8-week-old C57BL/6J wild-type and nude B6.Cg-foxn1nu/J mice. Animal experiments were carried out in accordance with the guidelines of the NIH and The Wistar Institute Institutional Animal Care and Use Committee (IACUC). Mice were injected with plasmid DNA in the tibialis anterior or quadricep muscles. In vivo electroporation was performed using a CELLECTRA adaptive constant-current EP device (Inovio Pharmaceuticals). Triangular 3-electrode arrays consisting of 26G solid stainless steel electrodes were used to deliver square-wave pulses. Two constant-current pulses were delivered at 0.1 A for 52 ms/pulse, separated with a 1-s delay between pulses. Mice were given either 100 or 300 µg plasmid DNA resuspended in water. The plasmids were co-formulated with recombinant hyaluronidase to enhance their intramuscular distribution. A maximum of 30 µL volume was used at each injection site. pVax-1 empty vector was used as a negative control for DMAbs. Blood was collected by submandibular bleeding for DMAb quantification and lipid panel analysis. Samples were collected until day 42 or 62.

Mouse Lipid Panel Analysis

Lipid panel analysis was carried out using a VITROS 350 Clinical Chemistry Analyzer. Mice were fasted for 4 hours and bled by submandibular bleeding. Serum samples collected from whole blood were used for the lipid panel analysis. Mouse non-HDL-C levels were calculated by subtracting HDL-C from total cholesterol.

Statistics

Experimental data were analyzed using two-way ANOVA tests. Differences were deemed significant at p values<0.05. All graphs were prepared using GraphPad Prism 6 software.

The results are now described.

Construction of Mouse Anti-PCSK9 DMAb Plasmids and In Vitro Characterization

Figure 2:
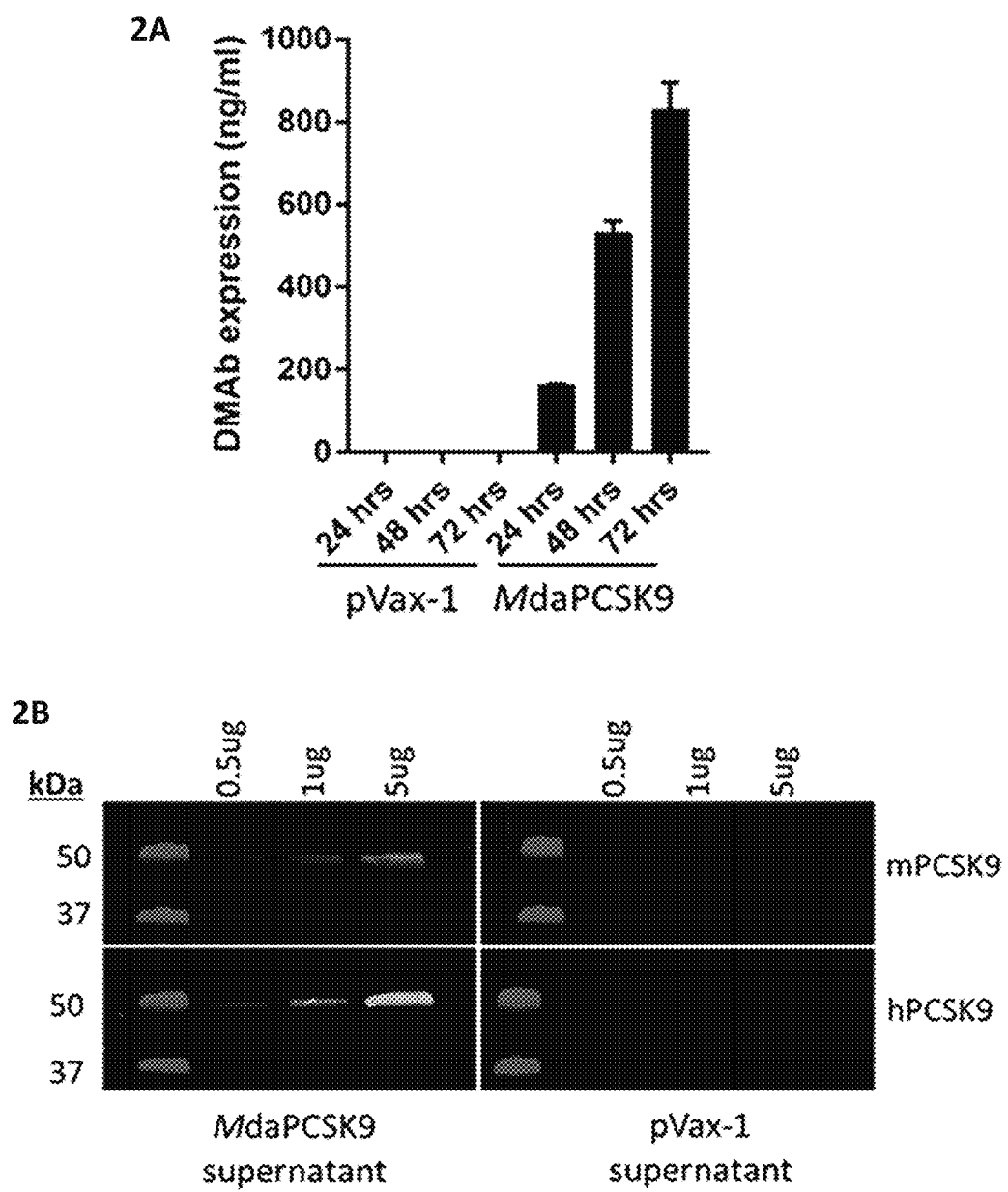
FIG. 2, comprising
Figure 2:
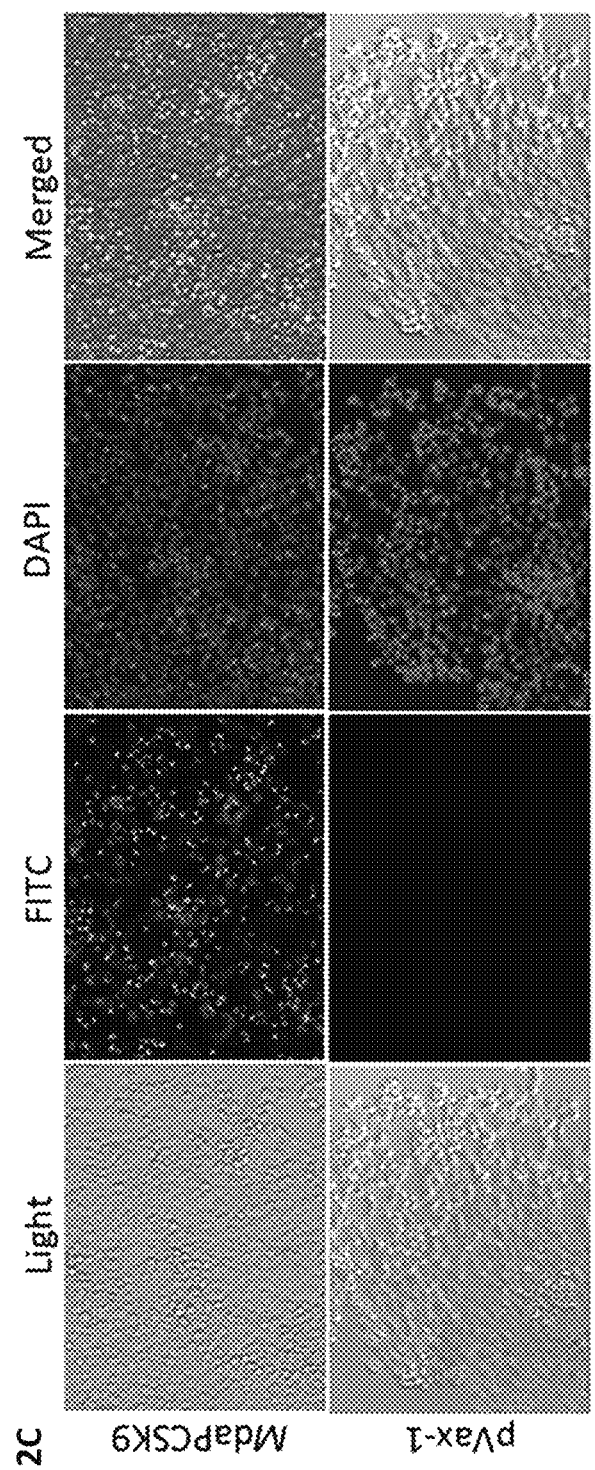

The mouse anti-PCSK9 (IgG2a) was designed in a single linked heavy- and light-chain cassette to be expressed from a single open reading frame, with the heavy- and light-chain genes separated by a previously developed furin/P2A cleavage site (FIG. 1B) to provide efficient protein processing necessary for immunoglobulin G (IgG) production in vivo. A cytomegalovirus (CMV) promoter in the pVax-1 vector was used to drive the expression of the antibodies, and the final construct was designated MdaPCSK9. At 72 hours after plasmid transfection into HEK293T cells, secreted antibody expression in supernatants was determined to be 831 ng/mL for MdaPCSK9 (FIG. 2A). Western blot-binding studies, using supernatants from MdaPCSK9 DMAb-transfected cells, showed specific binding to both human and mouse recombinant PCSK9 antigens, with greater binding detected to human PCSK9 (FIG. 2B). This showed proper binding activity of MdaPCSK9 against the PCSK9 antigen. Fluorescence microscopy was also used to demonstrate MdaPCSK9 expression in Hepa1-6 cells (FIG. 2C), and it showed a strong expression of MdaPCSK9 in DMAb plasmid-transfected, but not control, pVax1-transfected cells.

In Vivo Expression and Kinetics of MdaPCSK9

Figure 3:
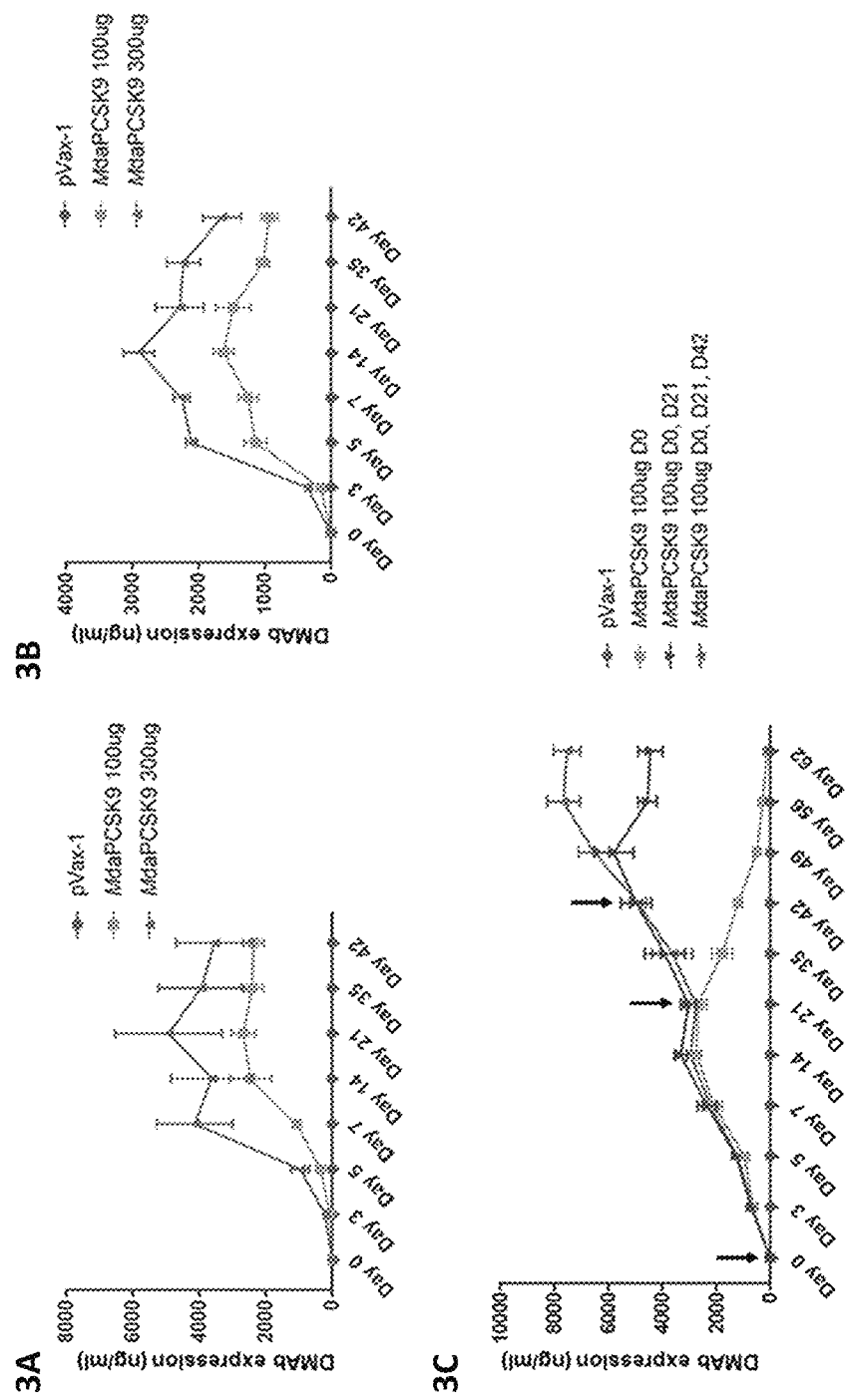
FIG. 3, comprising

The expression level and duration of the daPCSK9 DMAbs were evaluated in C57BL/6J wild-type and nude B6.Cg-foxn1nu/J mice (Jackson Laboratory) (FIG. 3). Plasmid DNA (100 or 300 µg) was injected intramuscularly into the tibialis anterior muscle, followed by electroporation (IM-EP). daPCSK9 with a mouse backbone demonstrated high expression with a long duration. MdaPCSK9 levels reached a maximum mean of 2,902 ng/mL at day 14, and they persisted for over 6 weeks, with blood levels at 1,649 ng/mL on day 42. In nude mice, the MdaPCSK9 expression was higher, reaching a maximum mean of 4,923 ng/mL at day 21, and expression persisted through the last bleed at day 42. Sequential administration of mouse DMAbs at days 0, 21, and 42 resulted in continuous increases in DMAb expression, with MdaPCSK9 levels reaching 7,521 ng/mL (3×100 µg doses) on day 62 (FIG. 3C). This highlights the sustainability of DMAb expression over long periods. Improved MdaPCSK9 expression was observed when doses were spread out over several-week periods, simplifying administration.

PCSK9 Protein Binding and Inhibition by DMAbs

PCSK9 inhibition was determined using western blot analysis of LDLR expression levels in mouse liver sections (FIG. 4A). Mouse livers were harvested at day 5, and the LDLR expression was evaluated by comparing the human and MdaPCSK9-treated mice to pVax-1 control mice. Western blot analysis showed that LDLR expression levels were significantly higher for PCSK9 DMAb-treated mice than control mice. ELISA protein quantification was used to detect the presence of DMAbs in the livers of treated mice. DMAb levels were 185 ng/mg tissue for MdaPCSK9 (FIG. 4B). Binding western blot analysis was used to evaluate the binding of DMAbs from serum samples of DMAb-treated and untreated mice to human and mouse PCSK9 protein (FIG. 4C). After incubation of the serum samples with blots containing the recombinant mouse or human PCSK9 proteins, the sera of DMAb-treated mice reacted with the PCSK9 protein, but sera from the pVax-1-treated mice did not. Furthermore, MdaPCSK9 were evaluated on a human liver cell line, Huh7; 72 hours after transfection, cells were harvested and analyzed by flow cytometry (FIG. 4D). There were significant increases in LDLR levels in the MdaPCSK9-treated group, with mean fluorescence intensity (MFI) increasing from 1,573 in the control group to 11,166 in the DMAb-treated group. The results demonstrate the functional efficacy of daPCSK9 at inhibiting PCSK9 protein from inducing LDLR degradation in hepatocytes.

Lipid-Lowering Capability of Mouse Anti-PCSK9 DMAb

Figure 5:
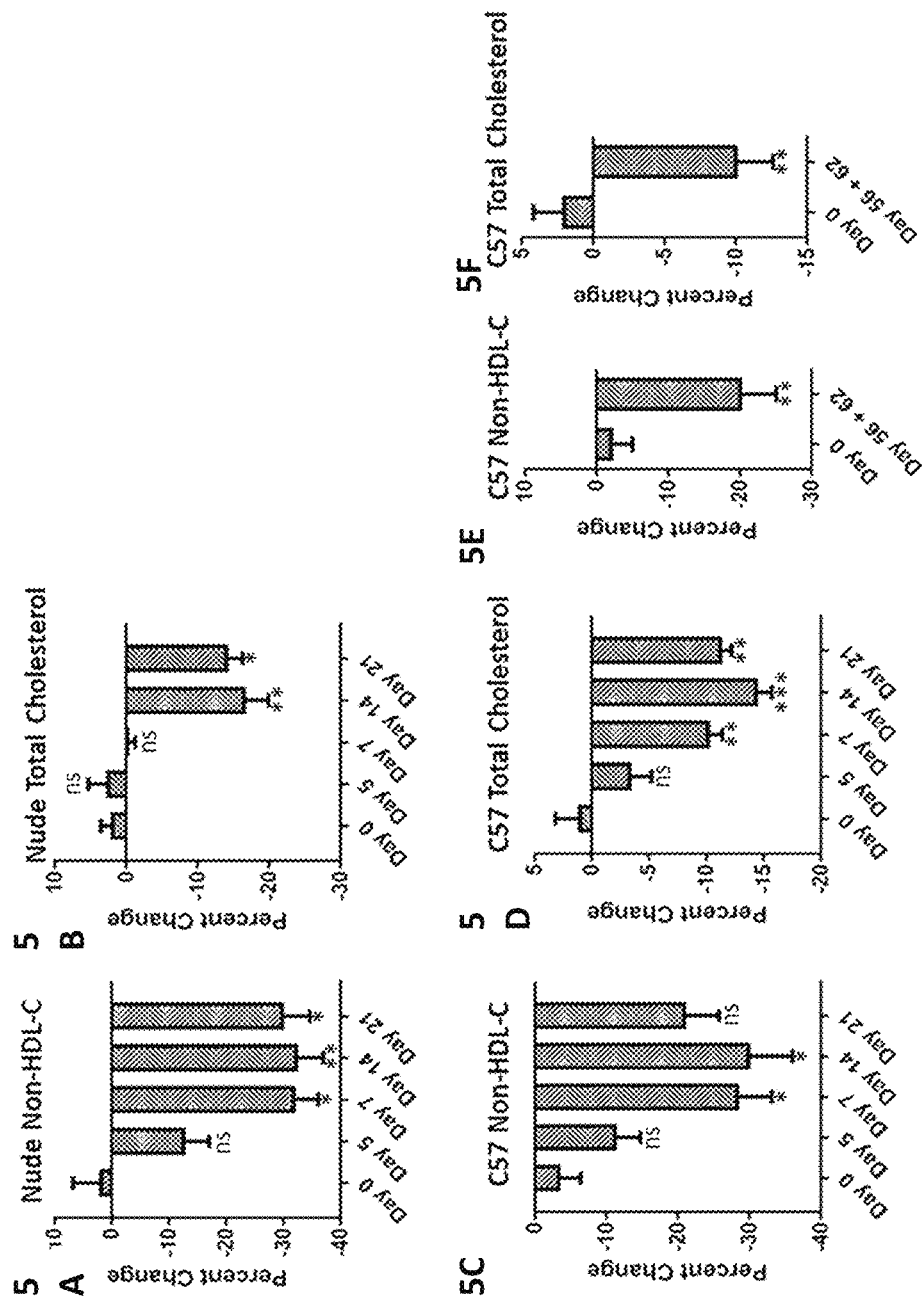
FIG. 5, comprising

The lipid-lowering capability of daPCSK9 was evaluated in C57BL/6J wild-type and B6.Cg-foxn1nu/J nude mice (FIG. 5). For accurate calculations of lipid reductions in the treated group, percentage decreases were analyzed against the control group for each day. In C57BL/6J mice, a significant 28.6% decrease in non-HDL-C was detected on day 7 for the MdaPCSK9 group. By day 14, there was a 30% decrease in non-HDL-C for the MdaPCSK9 group. Total cholesterol reductions were also observed for the MdaPCSK9 group, with a 14% decrease on day 14. In nude mice, there was a significant 32.5% reduction in non-HDL-C on day 14 for those treated with MdaPCSK9. This reduction persisted until day 21. There were similar reductions in total cholesterol that persisted to day 21, with a 14.3% decrease. The persistent reduction of non-HDL-C and total cholesterol in the mouse models correlates with the DMAb expression in the circulation. Repeated administrations of MdaPCSK9 led to increasing DMAb expression kinetics over a period of 62 days, with reductions in non-HDL-C of 20.9% from pooled sera on days 56 and 62 (FIGS. 5E and 5F).

Figure 7:
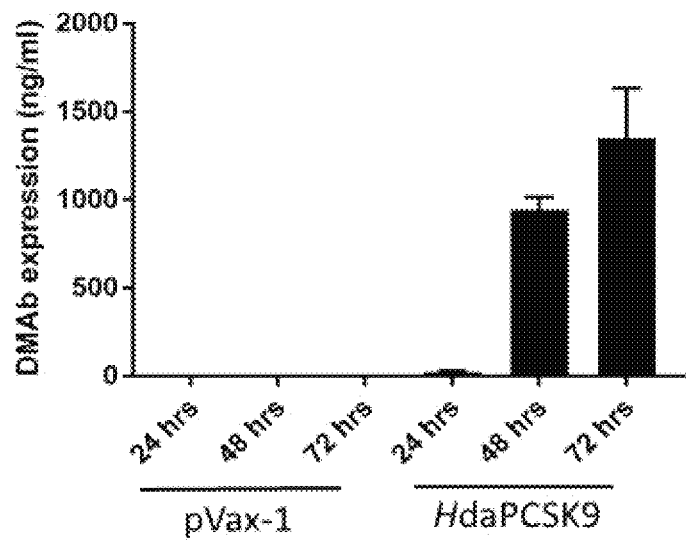
FIG. 7, comprising
Figure 7:
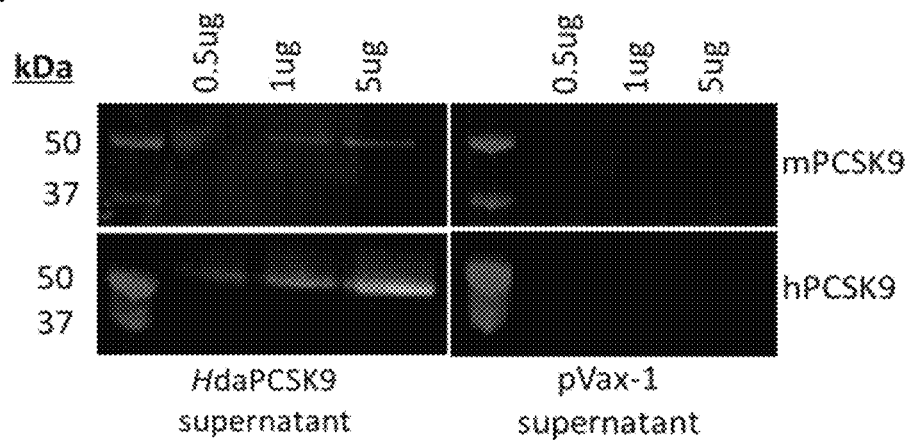
Figure 7:
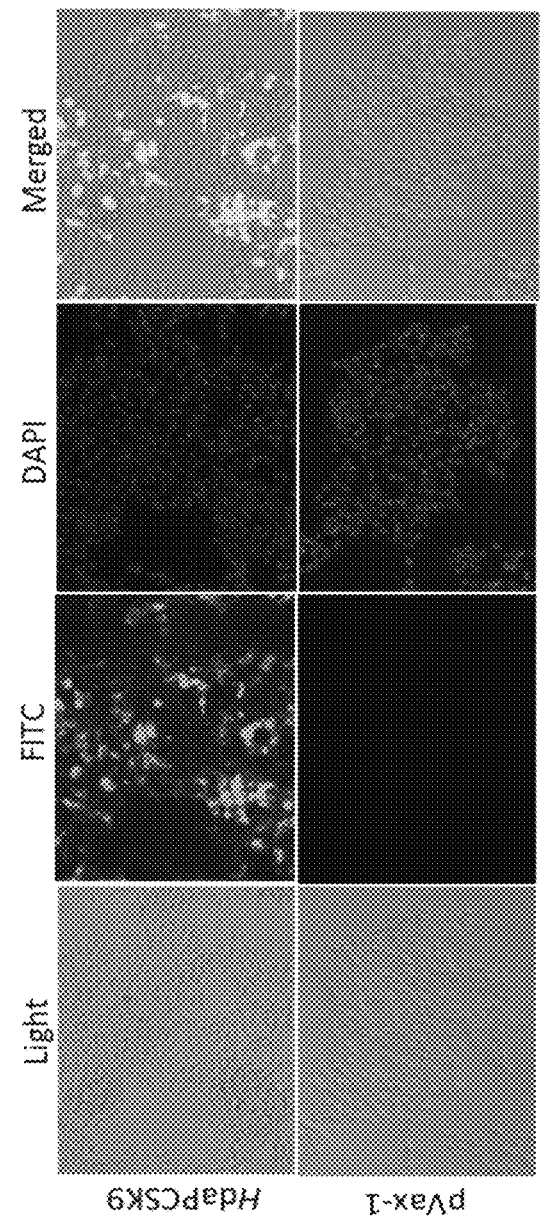

Construction and Evaluation of Human Anti-PCSK9 DMAb daPCSK9 plasmid engineered to express either human or mouse Fc regions (labeled HdaPCSK9 and MdaPCSK9, respectively) were designed to evaluate the effect on expression levels and kinetics in vivo. Evaluation of HdaPCSK9 in HEK293T cells showed the DMAb expression levels at 1,349 ng/mL (FIG. 7). Strong expression for HdaPCSK9 was also confirmed in Hepa1-6 cells by using fluorescence microscopy after intracellular staining with anti-human IgG-fluorescein isothiocyanate (FITC). Western blot-binding studies with the HdaPCSK9 demonstrated binding to both recombinant human and mouse PCSK9 proteins.

Figure 6:
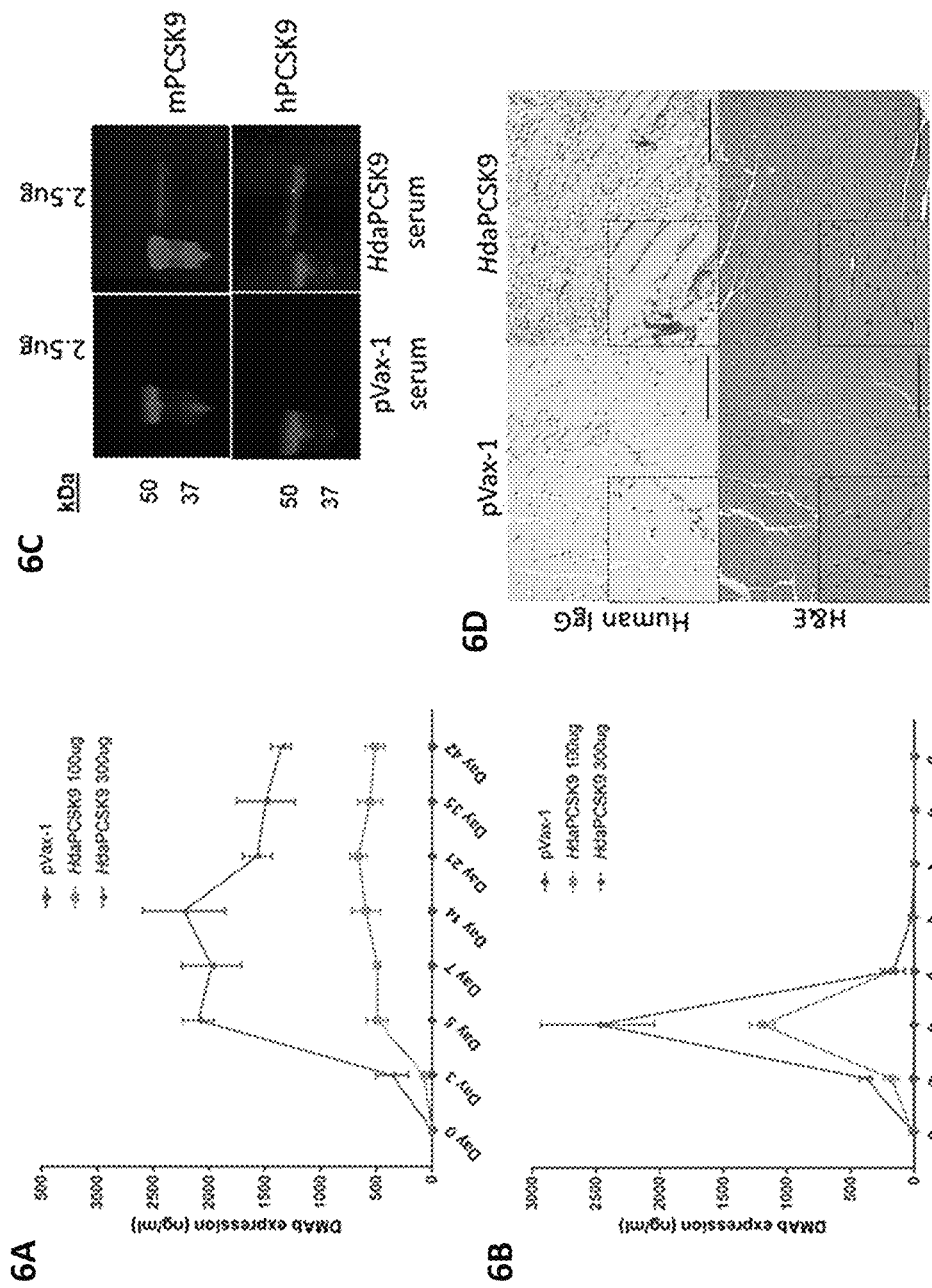
FIG. 6, comprising

HdaPCSK9 expression levels and kinetics were analyzed in vivo in wild-type C57BL/6J and nude B6.Cg-foxn1nu/J mice (FIGS. 6A and 6B). After a single intramuscular administration of 300 µg plasmid DNA, the HdaPCSK9 reached a maximum mean of 2,224 ng/mL protein mAbs at day 14 in nude mice. In wild-type mice, there was an acute immune reaction to the DMAbs containing human Fc, resulting in drops in DMAb expression by day 7. Maximum expression was observed at day 5, with a mean of around 2,485 ng/mL for the 300 µg dose of HdaPCSK9. The results of human DMAb studies in wild-type mice demonstrate the importance of considering intraspecies differences in antibody evaluation and how this may impact translation to other models. The reason for the resulting drop in expression of human PCSK9 DMAb is interesting. It is possible that immunogenicity or other factors could be involved, which will be investigated in future studies. The functional activity of sera DMAbs was confirmed by binding western blot analysis, showing binding to both recombinant mouse and human PCSK9 proteins (FIG. 6C).

Anti-PCSK9 DMAb expression was also confirmed in vivo by immunohistochemistry analysis of mouse muscle tissue at day 5. As shown in FIG. 6D, immunohistochemistry using HdaPCSK9 immuno-stained with anti-human IgG-horseradish peroxidase (HRP) indicates positive browning in the mouse tibialis anterior muscle section, compared to no browning in the control pVax-1 muscle sections. H&E staining of the DMAb-treated and control groups showed no signs of tissue damage. This confirms the expression of anti-PCSK9 DMAbs and the lack of tissue damage caused by their administration.

Lipid-Lowering Capability of Human Anti-PCSK9 DMAbs

Figure 8:
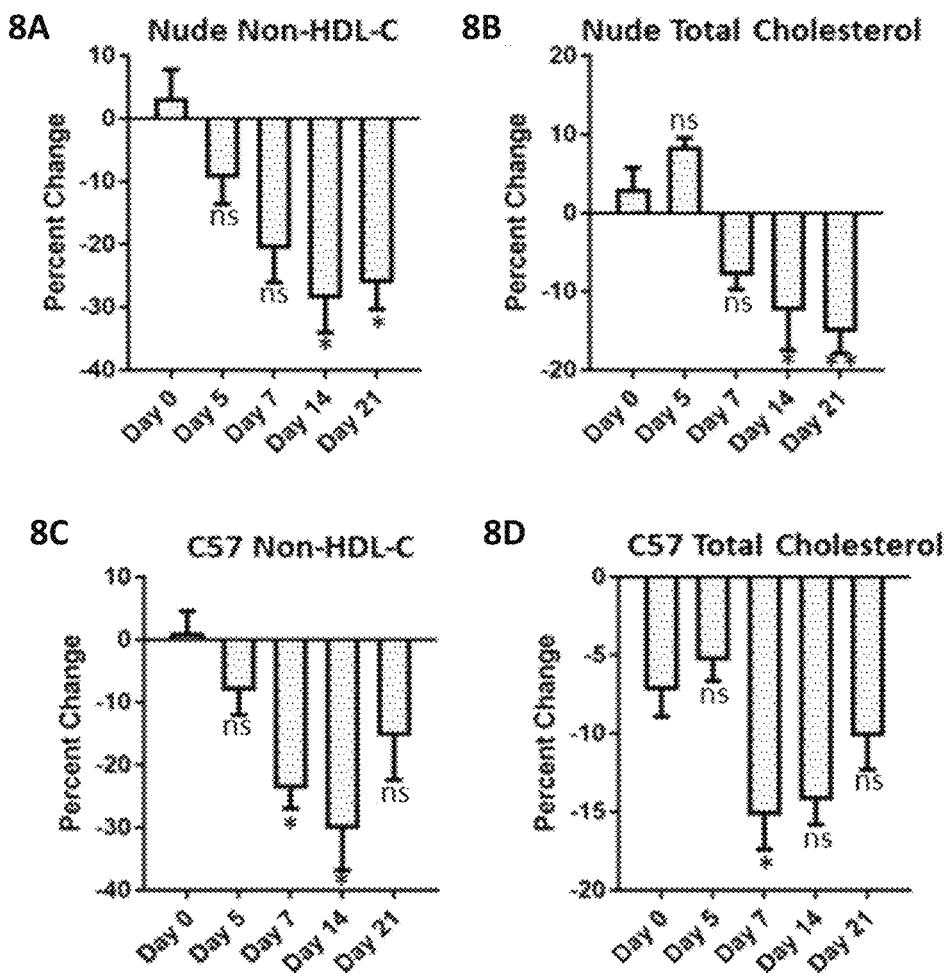
FIG. 8, comprising

The HdaPCSK9 performed similarly to MdaPCSK9 in its capacity at lipid reduction in C57BL/6J wild-type and B6.Cg-foxn1nu/J nude mice (FIG. 8). In wild-type mice, there was a significant 23.8% decrease in non-HDL-C detected on day 7 for the HdaPCSK9 group and a 30% reduction by day 14. Total cholesterol reduction was also observed, with a 14% decrease on day 14. Compared to HdaPCSK9, MdaPCSK9 demonstrated better reductions of both non-HDL-C and total cholesterol, which correlates with its superior expression levels and duration in the circulation in the matched species. In nude mice, there were significant reductions in non-HDL-C on day 14 for both species' antibodies, with 28.6% for human and 32.5% for mouse anti-PCSK9 DMAb groups. This reduction persisted until the final endpoint at day 21. There were similar reductions in total cholesterol that persisted until day 21, with a 15.2% decrease for the HdaPCSK9. Although they were not expressed as well in mouse as MdaPCSK9, the human DMAb performed well at lipid reduction in this short-term study supporting potential application of the human Fc DMAbs in a matched species setting.

Anti-PCSK9 DMAbs Reduce Non-HDL-C and Total Cholesterol

Individuals with elevated LDL-C or those afflicted with hereditary familial hypercholesterolemia are at increased risk for CHD. LDL-C reduction therapy with 3-hydroxy-3-methyl-glutaryl-coenzyme A (HMG-CoA) reductase inhibitors, such as statins, has been a standard treatment for reducing the risk of CHD, but intolerable musculoskeletal symptoms can prevent their use (Backes et al., 2017, J Clin Lipidol 11:24-33). Alternative therapies are needed when the gold standard for reducing high LDL-C causes such adverse effects. PCSK9 inhibitors are emerging as a potent important new approach for reducing LDL-C by increasing its hepatic clearance via the LDLR.

Several strategies have been taken to inhibit PCSK9, with mAbs achieving recent success. Evolocumab and alirocumab are two FDA-approved anti-PCSK9 recombinant mAbs that have shown significant LDL-C reduction. Various recombinant anti-PCSK9 antibodies have been investigated in mice for their lipid-lowering capabilities. A transgenic cholesteryl ester transfer protein(CETP)/LDLR-hemi mouse model has been developed that expressed human CETP transgene and one copy of the LDLR, to mimic healthy human lipid levels in mice (Zhang et al., 2012, Int. J. Biol Sci 8:310-27). After 48 hours of a single intravenous administration of the anti-PCSK9 antibody at 1.1 mg/kg, there was a 29% reduction from the baseline in LDL-C, with serum antibody levels of 3.5 µg/mL. This correlates with expression levels and the lipid reduction capability observed with the DMAbs. There was even a significant 50%-70% reduction in LDL-C at higher administered recombinant antibody doses of 3 mg/kg and 10 mg/kg (Zhang et al., 2012, Int. J. Biol Sci 8:310-27). Chan et al. evaluated an anti-PCSK9 antibody in wild-type mice and LDLR-knockout mice, and they observed a 36% reduction in total cholesterol 3 days after administration to the wild-type mice, while detecting no change in the LDLR-knockout mice (Chan et al., 2009, PNAS 106:9820-25). Another group examined the effect of an anti-PCSK9 antibody on humanized hyperlipidemic Pcsk9$^{hum/hum}$Ldlr$^{-/+}$ mice on a carbohydrate-rich diet. The anti-PCSK9 antibody REGN727 reduced LDL-C to a pre-diet level within 24 hr. It was also found to be effective in cynomolgus monkeys, with up to a 75% reduction in LDL-C for over 20 days after a single intravenous administration (Gusarova et al., 2012, Clin Lipidol 7:737-43).

Recombinant anti-PCSK9 mAbs have shown success, but a major limiting factor to their use is their high cost. Moreover, they require frequent dosing, such as every 2 weeks used for recombinant anti-PCSK9 antibody therapeutics. Here a novel approach to inhibit PCSK9 was developed using DMAb technology. DMAbs have several advantages that make them an important new technology for the development of protein-based therapeutics, such as cost-effectiveness, ease of manufacturing, stability, and no requirement for a cold chain and rapid development and engineering. DMAbs can be delivered via intramuscular or intradermal routes via in vivo electroporation of plasmid DNA. Low-voltage electroporation leads to consistent intracellular delivery of the injected plasmid DNA. The DMAb platform has shown protective efficacy against several viral pathogens, including HIV, Middle East Respiratory Syndrome (MERS), and Zika among others, and it is currently under evaluation for immuno-therapeutics against cancers (Flingai et al., 2015, Sci Rep 5:12616; Elliott et al., 2017, Vaccines 2:18; Muthumani et al., 2016, J Infect Dis 214: 369-78; Patel et al., 2017, Nat Commun 8:637; Muthumani et al., 2017, Cancer Immunol Immunother 66:1577-88).

In this study, a CELLECTRA in vivo electroporation device was used, which utilizes an adaptive constant current electroporation system that can measure tissue resistance and adjust in real time to prevent any tissue damage and enhance DNA uptake. For DNA delivery, electroporation has been able to allow 1,000-fold enhancement in gene expression in vivo. There have been several impactful clinical studies performed using this in vivo electroporation technology. One example is the human papilloma virus (HPV) VGX-3100 DNA vaccine, which showed efficacy in phase IIb clinical trials, demonstrating robust antigen-specific T cell response, as well as inducing clearance of the HPV virus and lesions (Trimble et al., 2015, Lancet 386: 2078-88). Another example is the development of the Zika virus DNA vaccine (Tebas et al., 2017, NEJM). In a phase I clinical trial evaluating the safety and immunogenicity of DNA vaccine GLS-5700, healthy adults demonstrated development of both binding and neutralizing antibodies, associated with protection in animal models (Tebas et al., 2017, NEJM).

In this study, the mouse PCSK9 DMAb was capable of expression for over 42 days in wild-type mice. Expression for several months has been demonstrated with several DMAbs, such as Anti-Dengue (Flingai et al., 2015, Sci Rep 5:12616), Anit-Ebola, and the immunoadhesin eCD4-Ig (Xu et al., 2018, EBioMedicine 34:97-105). These studies support the potential of DMAbs, some lasting several months, to be administered as a possible treatment for atherosclerotic cardiovascular disease. Here the efficacy of the anti-PCSK9 DMAb platform was evaluated for its ability to express anti-PCSK9 antibodies directly in vivo and to exhibit lipid-lowering properties in mice. An anti-PCSK9 DMAb (MdaPCSK9) that used a mouse-matched backbone was found to express for at least 6 weeks in vivo at reasonable levels. Importantly, inhibition of PCSK9 was observed in vivo, showing elevated liver LDLR expression 5 days after treatment. With a single intramuscular administration of anti-PCSK9 DMAbs (300 µg plasmid DNA), reductions in non-HDL-C and total cholesterol were observed with both mouse and human anti-PCSK9 antibodies. Significant reductions in non-HDL-C were observed with MdaPCSK9 as early as day 7 post-administration in wild-type and nude mice. Compared to wild-type pVax-1 negative controls, there was a 28.6% reduction on day 7 for the MdaPCSK9 group. Both human and mouse anti-PCSK9 DMAbs led to 30% decreases in non-HDL-C and 14% reductions in total cholesterol by day 14. Wild-type mice, which are normo-cholesterolemic, were used in the current study, and it is difficult to observe significant decreases in LDL levels in these mice as compared to transgenic hypercholesterolemic mice. Future studies with transgenic hypercholesterolemic mice are important for evaluation of the PCSK9 DMAbs.

In conclusion, these results demonstrate the efficacy of highly novel anti-PCSK9 DMAbs at reducing non-HDL-C and total cholesterol, and they suggest the potential of this new technology in the treatment of atherosclerotic cardiovascular disease and familial hypercholesterolemia patients. These novel DNA-produced, antibody-based therapeutics could be valuable as an alternative method of therapy of treatment for hypercholesterolemia and other cardiovascular diseases.

Example 2

Engineering of DNA-Encoded PCSK9 Monoclonal Antibodies as Novel Lipid-Lowering Therapeutics The data presented herein demonstrates an anti-PCSK9 DNA-encoded monoclonal antibody (DMAb) that is a suitable alternative to protein-based lipid-lowering therapeutics. The data demonstrates successful suppression of PCSK9 in vivo and elevation of liver LDLR levels in DMAb-treated mice.

DMAbs allow for a more cost-effective and potent pharmacologic intervention threfore making the therapeutics more affordable and available for high-risk cardiovascular patients. DMAb technology is an alternative form of antibody therapy where the plasmid DNA-encoding the monoclonal antibody is delivered to body to express the antibody in vivo, instead of the costlier path of recombinant protein-based antibody management because recombinant mAb protein production techniques are laborious (folding, glycosylation pattern, yield, and purification challenges), time-consuming, and expensive. Therefore, DMAbs are more cost effective, more stable, are easier to manipulate, can be delivered multiple times without any anti-vector response, require fewer number of treatments and do not require a cold-chain distribution as compared to recombinant mAbs.

An in vivo electroporation device is used to intracellular delivery of PCSK9 DMAb plasmid. The DNA-encoded PCSK9 monoclonal antibodies re expressed intramuscularly and subsequently PCSK9 DMAbs are released into circulation. PCSK9 DMAbs migrate to the liver where they bind and inhibit PCSK9. LDL binding to LDLR results in uptake and degradation of LDL and recycling of LDLR, PCSK9 binds LDLR, resulting in LDLR degradation, and PCSK9 DMAb inhibits PCSK9, allowing for increased LDLR recycling and display on cell surface (FIG. 1).

PCSK9 DMAb with mouse backbone demonstrated the high expression with the long duration, persisting for 42 days in wild type mice (FIG. 3). Single intramuscular administration of PCSK9 DMAb plasmid DNA was able to lead to significant reduction in non-HDL and total cholesterol in mice. A substantial 28.6% decrease in non-HDL and 10.3% decrease in total cholesterol by day 7 in wild type mice was achieved with mouse PCSK9 DMAb.

Remarkably, repeat dose administration of mouse PCSK9 DMAb at days 0, 21, and 42 led to increasing expression kinetics, with DMAb levels of around 7521.3 ng/ml (3×100 ug doses) at day 62. This highlights the sustainability of DMAb expression over long period. (FIG. 3).

Figure 4:
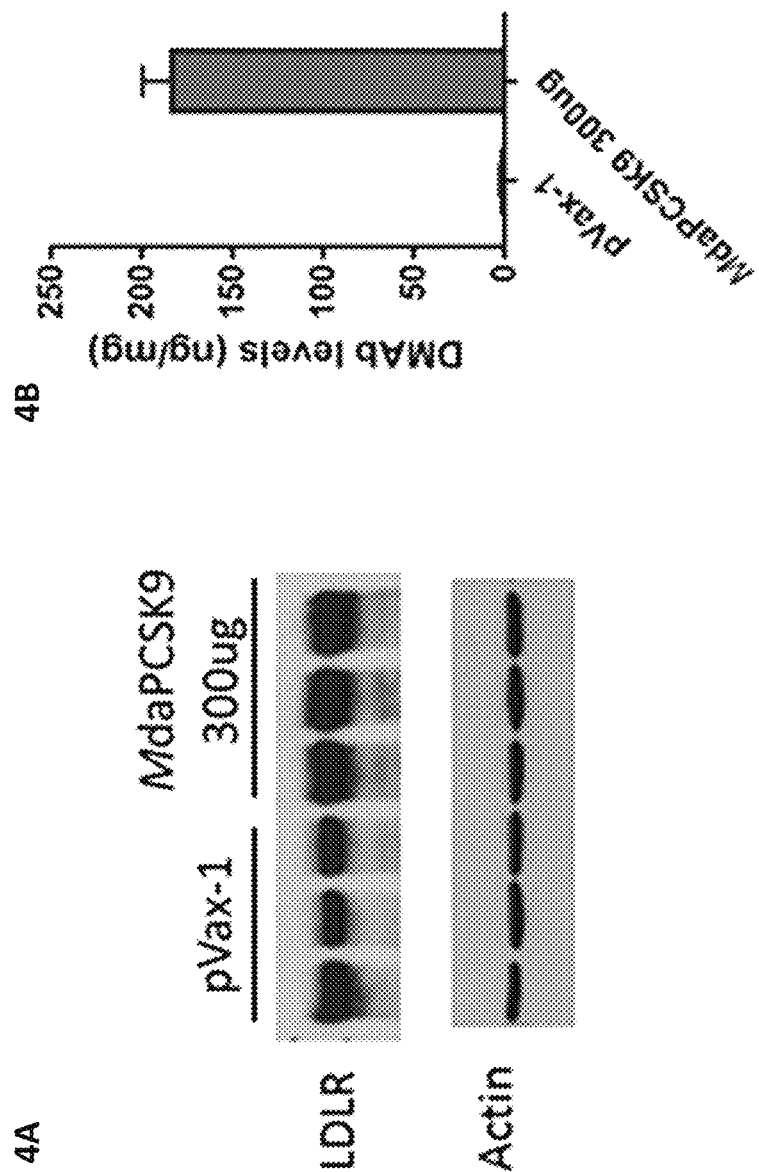
FIG. 4, comprising
Figure 4:
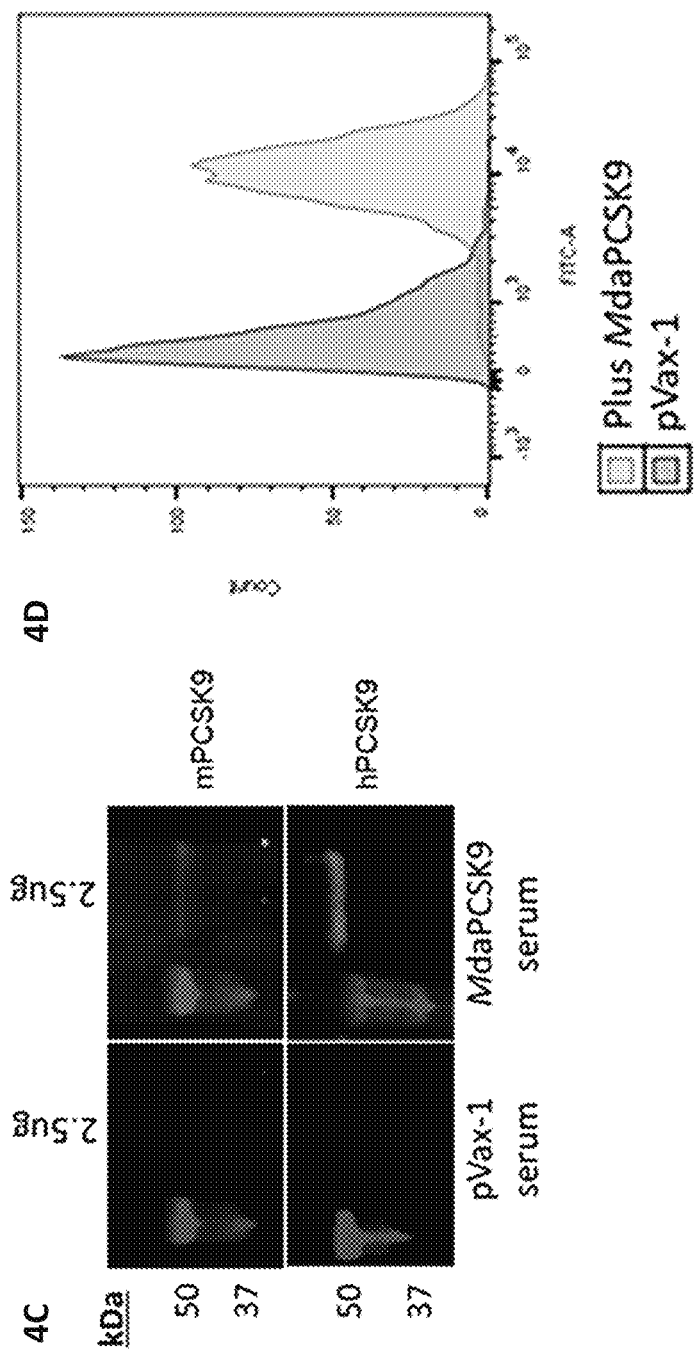
Figure 4:
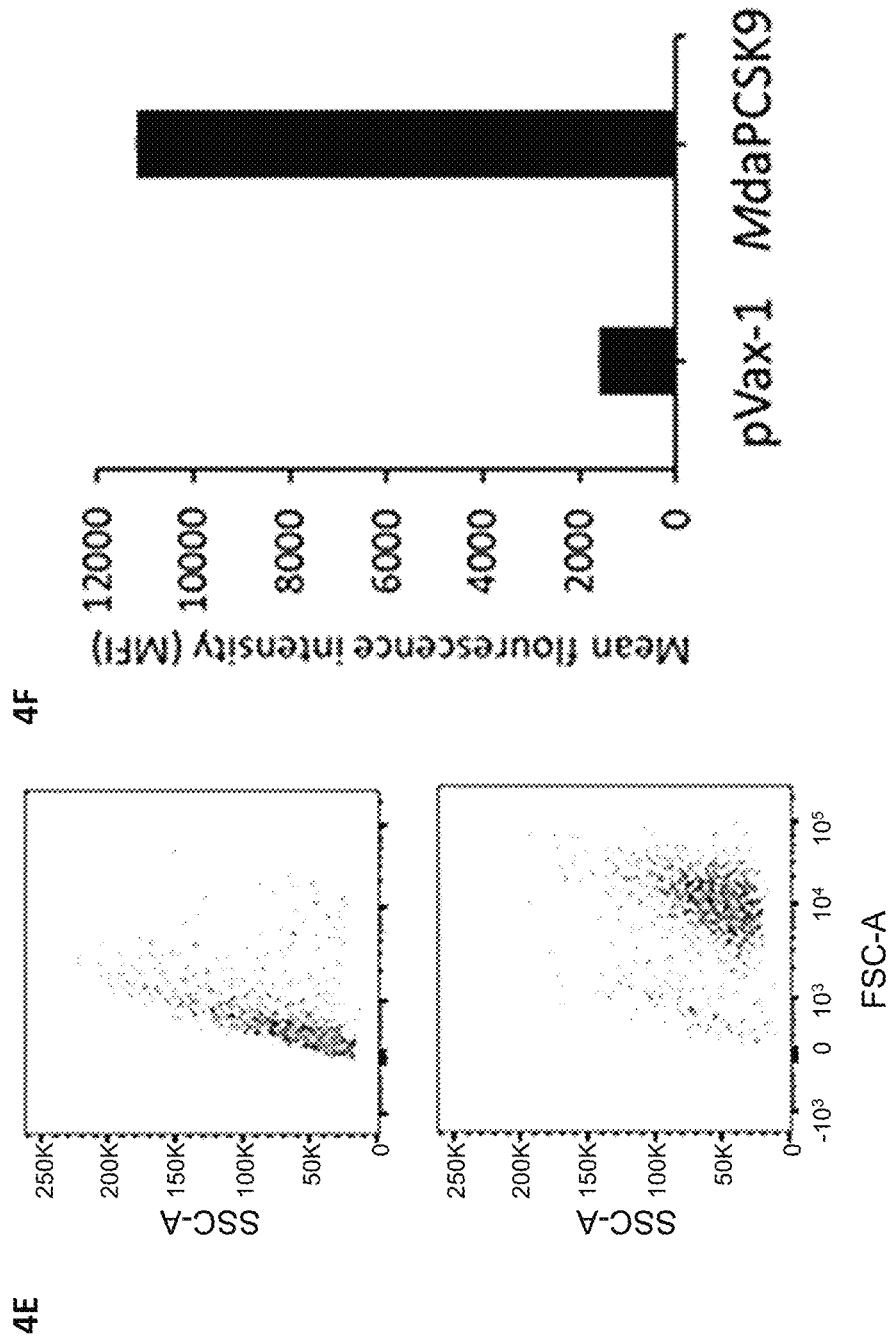

Western blot analysis demonstrated significant increase in the LDLR expression levels in PCSK9 DMAb-treated mice compared to control mice. The presence of DMAbs were also detected in the liver of treated mice with levels of around 185.2 ng/mg tissue for mouse PCSK9 DMAb. (FIG. 4).

Mouse PCSK9 DMAb demonstrated significant reduction for both non-HDL and total cholesterol, which correlates with its superior expression and duration levels in circulation. We achieved a substantial 28.6% decrease in non-HDL and 10.3% decrease in total cholesterol by day 7 in wild type mice with mouse PCSK9 DMAb. (FIG. 5)

Remarkably, repeat dose administration of mouse PCSK9 DMAb led 20.9% reduction in non-HDL at days 56 and 62 (FIG. 5).

PCSK9 inhibitors have emerged emerging as potent alternative approach for reducing LDL-C by increasing their hepatic clearance via the LDL receptor. Patients unable to tolerate statins are great candidates for PCSK9 inhibitors. The data presented herein demonstrates the engineering of PCSK9 DNA-encoded monoclonal antibody (DMAb) platform and its potential at inhibiting PCSK9 and its lipid-lowering properties in mice. Successful inhibition of PCSK9 was observed in vivo, showing elevated liver LDLR expression five days after treatment. Significant reduction in non-HDL and total cholesterol was detected as early as day 7. The PCSK9 DMAb expression and lipid reduction capacity was demonstrated over long period, with persistence even at Day 62. These DNA-produced, antibody-based therapeutics could provide an alternative, more cost-effective approach to reducing LDL-C, overcoming the challenges associated with recombinant protein-based monoclonal antibody therapeutics.

DNA-encoded monoclonal antibody-based therapeutics could provide a novel, more cost-effective approach to reducing LDL-C, overcoming the challenges associated with recombinant protein-based monoclonal antibody therapeutics. The DMAb technology could considerably advance the field of immunotherapeutics for treatment of atherosclerosis and numerous other diseases.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for generating one or more anti-PCSK9 antibodies or antigen-binding fragments thereof in a subject, comprising one or more nucleic acid molecules encoding one or more anti-PCSK9 antibodies or antigen-binding fragments thereof;
wherein the composition comprises:
a) a nucleotide sequence encoding an amino acid sequence having at least about 99% identity over the entire length of at least one amino acid sequence selected from the group of SEQ ID NOs: 1, 3, 5 and 7, wherein the encoded CDRs comprises 100% identity to the CDRs of SEQ ID NO: 1, 3, 5 or 7;
b) a nucleotide sequence having at least about 99% identity over the entire length of at least one nucleotide sequence selected from the group of SEQ ID NOs: 2, 4, 6 and 8, wherein the nucleotide sequences encoding the CDRs comprises 100% identity to the CDR coding sequences of SEQ ID NO:2, 4, 6 and 8; or c) any combination thereof.

2. The composition of claim 1, comprising a nucleotide sequence encoding a cleavage domain.

3. The composition of claim 1, comprising a nucleotide sequence encoding a variable heavy chain region and a variable light chain region of the antibody.

4. The composition of claim 1, comprising a nucleotide sequence encoding a polypeptide comprising a constant heavy chain region and a polypeptide comprising a constant light chain region.

5. The composition of claim 1, comprising a nucleotide sequence encoding a polypeptide comprising a variable heavy chain region; a constant heavy chain region; a cleavage domain; a variable light chain region; and a constant light chain region.

6. The composition of claim 1, wherein the nucleotide sequence encodes a leader sequence.

7. The composition of claim 1, comprising a nucleotide sequence encoding at least one amino acid sequence selected from the group of SEQ ID NOs: 1, 3, 5 and 7.

8. The composition of claim 1, comprising a nucleotide sequence having at least about 98% identity over the entire length of at least one nucleotide sequence selected from the group of SEQ ID NOs: 2, 4, 6 and 8.

9. The composition of claim 1, wherein the one or more nucleic acid molecules are engineered to be in an expression vector.

10. The composition of claim 9, further comprising a pharmaceutically acceptable excipient.

11. A method of treating a disease in a subject, the method comprising administering to the subject a composition of claim 1.

12. The method of claim 11, wherein the disease is cardiovascular disease or hypercholesterolemia.

13. A method for decreasing an LDL-C in a subject in need thereof, the method comprising administering a composition of claim 1 to the subject.

14. The method of claim 13, wherein administering the composition comprises an electroporating step.

* * * * *